United States Patent
Dobosy et al.

(10) Patent No.: US 11,999,994 B2
(45) Date of Patent: Jun. 4, 2024

(54) METHODS FOR PRODUCTION AND QUANTIFICATION OF UNIQUE MOLECULAR IDENTIFIER-LABELED BEADS

(71) Applicant: INTEGRATED DNA TECHNOLOGIES, INC., Coralville, IA (US)

(72) Inventors: Joseph Dobosy, Coralville, IA (US); Scott D. Rose, Coralville, IA (US); Jeffrey A. Manthey, North Liberty, IA (US); Shawn D. Allen, Williamsburg, IA (US); Steven A. Henck, Mountain View, CA (US); Mark Behlke, Coralville, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 123 days.

(21) Appl. No.: 17/574,842

(22) Filed: Jan. 13, 2022

(65) Prior Publication Data

US 2022/0220545 A1    Jul. 14, 2022

Related U.S. Application Data

(60) Provisional application No. 63/137,264, filed on Jan. 14, 2021.

(51) Int. Cl.
| | |
|---|---|
| C07H 21/04 | (2006.01) |
| C12N 15/113 | (2010.01) |
| C12Q 1/6837 | (2018.01) |
| C12Q 1/6876 | (2018.01) |

(52) U.S. Cl.
CPC .......... *C12Q 1/6837* (2013.01); *C12N 15/113* (2013.01); *C12Q 1/6876* (2013.01); *C12N 2310/11* (2013.01); *C12N 2310/3519* (2013.01); *C12N 2320/11* (2013.01)

(58) Field of Classification Search
None
See application file for complete search history.

(56) References Cited

U.S. PATENT DOCUMENTS

2016/0145683 A1*  5/2016  Fan .................. C12Q 1/6876
                                                              506/26
2018/0071705 A1   3/2018  Weitz et al.

FOREIGN PATENT DOCUMENTS

| EP | 3382034 A1 | 10/2018 |
|---|---|---|
| WO | 1990012111 A1 | 10/1990 |
| WO | 2020028882 A1 | 2/2020 |

OTHER PUBLICATIONS

Zilionis et al., "Single-cell barcoding and sequencing using droplet microfluidics," Nature Protocols, 2017, vol. 12, No. 1, pp. 44-73.
International Search Report and Written Opinion for Application No. PCT/US2022/012234 dated Apr. 25, 2022 (16 pages).

* cited by examiner

*Primary Examiner* — Kimberly Chong
(74) *Attorney, Agent, or Firm* — Michael Best & Friedrich LLP

(57) ABSTRACT

Described herein are compositions and methods for the production and quantification of barcoded or unique molecular identifier (UMI)-labeled substrates. In one aspect, the substrate is a bead comprising a template oligonucleotide that is elongated by successive extension reactions to provide a bead with an oligonucleotide comprising a plurality of barcodes and conserved anchor regions. Methods are also described for quantifying the amount of template oligonucleotide loaded onto the substrate and the products of the extension reaction after each round and after the final extension.

32 Claims, 5 Drawing Sheets

Specification includes a Sequence Listing.

384 × 384 × 384 = 56 million different barcodes

Exemplary Product Sequence:

TTTTTTAAGCAGUGGTATCCAACGCAGCCATTGAAGATCGATGGAGTGGAT
Loading sequence   Anchor-1   Barcode-1   Anchor-2   Barcode-2

CATCGATCGATTGGTTCTCACGTANNNNNNNNNVTTTTTTTT...
Anchor-3   Barcode-3   Anchor-4   N-domain      poly-T capture domain

FIG. 2C

Bead-Oligonucleotide Template
BEAD-5'-TATTAATTAATATATUAAGCAGTGGTATCAACGCAGAGTAC-3' (e.g., SEQ ID NO: 34)

Extension 1
5'-TATTAATTAATATATUAAGCAGTGGTATCAACGCAGAGTACCCATTGAAGATCGATG-3'
Primer 1 (e.g., SEQ ID NO: 1) 3'-x-GTCTCATGGGTAACTTCTAGCTAC-5'

Extension 2
5'-TATTAATTAATATATUAAGCAGTGGTATCAACGCAGAGTACCCATTGAAGATCGATGGAGTGGATTACGTGAG-3'
Primer 2 (e.g., SEQ ID NO: 11)         3'-x-CTAGCTACCTCACCTAATGCACTC-5'

Extension 3
5'-TATTAATTAATATATUAAGCAGTGGTATCAACGCAGAGTACCCATTGAAGATCGATGGAGTGGATTACGTGAGGATTGGTTCGTGATAC-3'
Primer 3 (e.g., SEQ ID NO: 21)                 3'-x-ATGCACTCCTAACCAAGCACTATG-5'

Extension 4
5'-CCCATTGAAGATCGATGGAGTGGATTACGTGAGGATTGGTTCGTGATACNNNNNNNNNNNVTTTTTTTTTTTTTTTTTTTTTT-3'
Primer 4 (e.g., SEQ ID NO: 31)         3'-x-GCACTATGNNNNNNNNNNNNNBAAAAAAAAAAAAAAAAAAAAAAA-5'

Final Extension Product
BEAD-5'-TATTAATTAATATATUAAGCAGTGGTATCAACGCAGAGTACCCATTGAAGATCGATGGAGTGGATTACGTGAGGATTGGTTCGTGATAC
NNNNNNNNNNNVTTTTTTTTTTTTTTTTTTTTTT-3' (SEQ ID NO: 39)

SEQUENCE LISTING

```
<160> NUMBER OF SEQ ID NOS: 41

<210> SEQ ID NO 1
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 1
catcgatctt caatgggtac tctg                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 2
catcgatccg gaaatcgtac tctg                                          24

<210> SEQ ID NO 3
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 3
```
catcgatcgt gcgactgtac tctg                                          24

<210> SEQ ID NO 4
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 4
catcgatcag actagagtac tctg                                          24

<210> SEQ ID NO 5
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 5
catcgatcgg ttaggtgtac tctg                                          24

<210> SEQ ID NO 6
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 6
catcgatcaa tgttccgtac tctg                                          24

<210> SEQ ID NO 7
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 7
catcgatcgg ttcctcgtac tctg                                          24

<210> SEQ ID NO 8
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 8

-continued catcgatcag caagaagtac tctg                                          24

<210> SEQ ID NO 9
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 9
catcgatcag cacgtagtac tctg                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 3'-terminus blocker

<400> SEQUENCE: 10
catcgatcgc gactctgtac tctg                                          24

<210> SEQ ID NO 11
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 11
ctcacgtaat ccactccatc gatc                                          24

<210> SEQ ID NO 12
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 12
ctcacgtacg atcttacatc gatc                                          24

<210> SEQ ID NO 13
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 13
ctcacgtact cgtgaacatc gatc                                          24

<210> SEQ ID NO 14
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 14
ctcacgtatg aatgcgcatc gatc                                          24

<210> SEQ ID NO 15
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 15
ctcacgtagt tagatccatc gatc                                          24

<210> SEQ ID NO 16
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 16
ctcacgtata agtccacatc gatc                                          24

<210> SEQ ID NO 17
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 17
ctcacgtact agcgaacatc gatc                                          24

<210> SEQ ID NO 18
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

```
<400> SEQUENCE: 18
ctcacgtacg catttccatc gatc                                              24

<210> SEQ ID NO 19
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 19
ctcacgtaca ggtgtacatc gatc                                              24

<210> SEQ ID NO 20
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 20
ctcacgtagg tcaacgcatc gatc                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 21
gtatcacgaa ccaatcctca cgta                                              24

<210> SEQ ID NO 22
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 22
gtatcacgca ccaaggctca cgta                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker
```

<400> SEQUENCE: 23
gtatcacgtt tccaacctca cgta                                             24

<210> SEQ ID NO 24
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 24
gtatcacgtc cgaatgctca cgta                                             24

<210> SEQ ID NO 25
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 25
gtatcacggc aattgactca cgta                                             24

<210> SEQ ID NO 26
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 26
gtatcacgaa cctagactca cgta                                             24

<210> SEQ ID NO 27
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 27
gtatcacgca ttcagtctca cgta                                             24

<210> SEQ ID NO 28
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)

```
<223> OTHER INFORMATION: 3'-terminus blocker

<400> SEQUENCE: 28
gtatcacggc gcatttctca cgta                                          24

<210> SEQ ID NO 29
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 29
gtatcacgca cttacgctca cgta                                          24

<210> SEQ ID NO 30
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: 3'-terminus blocker

<400> SEQUENCE: 30
gtatcacgca tgttcgctca cgta                                          24

<210> SEQ ID NO 31
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (31)..(31)
<223> OTHER INFORMATION: B is any nucleotide except A
<220> FEATURE:
<221> NAME/KEY: misc_feature
<222> LOCATION: (32)..(43)
<223> OTHER INFORMATION: N is any nucleotide
<220> FEATURE:
<221> NAME/KEY: misc_feature
<222> LOCATION: (51)..(51)
<223> OTHER INFORMATION: 3'-terminus blocker

<400> SEQUENCE: 31
aaaaaaaaaa aaaaaaaaaa aaaaaaaaaa bnnnnnnnnn nnngtatcac g            51

<210> SEQ ID NO 32
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-Amino-Sp18, hexaethylene glycol spacer
      (methylated phosphoramidite)

<400> SEQUENCE: 32
tttttttaag cagtggtatc aacgcagagt ac                                 32
```

```
<210> SEQ ID NO 33
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Deoxyribouridine

<400> SEQUENCE: 33
tttttttaag caguggtatc aacgcag                                          27

<210> SEQ ID NO 34
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Deoxyribouridine

<400> SEQUENCE: 34
tattaattaa tatuaagcag tggtatcaac gcagagtac                             39

<210> SEQ ID NO 35
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-flurophore
<220> FEATURE:
<221> NAME/KEY: misc_feature
<222> LOCATION: (17)..(17)
<223> OTHER INFORMATION: 3'-fluorescent quencher

<400> SEQUENCE: 35
ctgcgttgat accactg                                                     17

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
tttttttttt tttttttttt                                                  20

<210> SEQ ID NO 37
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5'-flurophore
<220> FEATURE:
<221> NAME/KEY: misc_feature
<222> LOCATION: (25)..(25)
<223> OTHER INFORMATION: 3'-fluorescent quencher
```

<400> SEQUENCE: 37
ctagtaaaaa aaaaaaaaaa actag                                          25

<210> SEQ ID NO 38
<211> LENGTH: 125
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: Loading Sequence
<220> FEATURE:
<221> NAME/KEY: misc_feature
<222> LOCATION: (13)..(39)
<223> OTHER INFORMATION: 27-mer Anchor-1
<220> FEATURE:
<221> NAME/KEY: misc_feature
<222> LOCATION: (14)..(4)
<223> OTHER INFORMATION: deoxyuridine
<220> FEATURE:
<221> NAME/KEY: misc_feature
<222> LOCATION: (40)..(47)
<223> OTHER INFORMATION: Varable Barcode-1
<220> FEATURE:
<221> NAME/KEY: misc_feature
<222> LOCATION: (48)..(55)
<223> OTHER INFORMATION: Anchor-2
<220> FEATURE:
<221> NAME/KEY: misc_feature
<222> LOCATION: (56)..(63)
<223> OTHER INFORMATION: Variable Barcode-2
<220> FEATURE:
<221> NAME/KEY: misc_feature
<222> LOCATION: (64)..(71)
<223> OTHER INFORMATION: Anchor-3
<220> FEATURE:
<221> NAME/KEY: misc_feature
<222> LOCATION: (72)..(79)
<223> OTHER INFORMATION: Variable Barcode-3
<220> FEATURE:
<221> NAME/KEY: misc_feature
<222> LOCATION: (80)..(87)
<223> OTHER INFORMATION: Anchor-4
<220> FEATURE:
<221> NAME/KEY: misc_feature
<222> LOCATION: (88)..(100)
<223> OTHER INFORMATION: N-domain
<220> FEATURE:
<221> NAME/KEY: misc_feature
<222> LOCATION: (101)..(125)
<223> OTHER INFORMATION: poly-T region (variable length)

<400> SEQUENCE: 38
tattaattaa tatuaagcag tggtatcaac gcagagtacn nnnnnnngat cgatgnnnnn      60
nnncatcgat cnnnnnnnnc tcacgtannn nnnnnnnnnv tttttttttt tttttttttt     120
ttttt                                                                125

<210> SEQ ID NO 39
<211> LENGTH: 125
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: Loading sequence
<220> FEATURE:
<221> NAME/KEY: misc_feature
<222> LOCATION: (13)..(39)

```
<223> OTHER INFORMATION: 27-mer anchor
<220> FEATURE:
<221> NAME/KEY: misc_feature
<222> LOCATION: (14)..(14)
<223> OTHER INFORMATION: deoxyribouridine
<220> FEATURE:
<221> NAME/KEY: misc_feature
<222> LOCATION: (40)..(47)
<223> OTHER INFORMATION: Variable Barcode-1
<220> FEATURE:
<221> NAME/KEY: misc_feature
<222> LOCATION: (48)..(55)
<223> OTHER INFORMATION: Anchor-2
<220> FEATURE:
<221> NAME/KEY: misc_feature
<222> LOCATION: (56)..(63)
<223> OTHER INFORMATION: Variable Barcode-2
<220> FEATURE:
<221> NAME/KEY: misc_feature
<222> LOCATION: (64)..(71)
<223> OTHER INFORMATION: Anchor-3
<220> FEATURE:
<221> NAME/KEY: misc_feature
<222> LOCATION: (72)..(79)
<223> OTHER INFORMATION: Variable Barcode-3
<220> FEATURE:
<221> NAME/KEY: misc_feature
<222> LOCATION: (88)..(100)
<223> OTHER INFORMATION: N-domain
<220> FEATURE:
<221> NAME/KEY: misc_feature
<222> LOCATION: (101)..(125)
<223> OTHER INFORMATION: poly-T region (variable length)

<400> SEQUENCE: 39
tattaattaa tatuaagcag tggtatcaac gcagagtacc cattgaagat cgatggagtg      60
gattacgtga ggattggttc gtgatacnnn nnnnnnnnnv tttttttttt tttttttttt     120
ttttt                                                                 125

<210> SEQ ID NO 40
<211> LENGTH: 125
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(12)
<223> OTHER INFORMATION: Loading Sequence
<220> FEATURE:
<221> NAME/KEY: misc_feature
<222> LOCATION: (13)..(39)
<223> OTHER INFORMATION: 27-mer Anchor-1
<220> FEATURE:
<221> NAME/KEY: misc_feature
<222> LOCATION: (14)..(14)
<223> OTHER INFORMATION: deoxyribouridine
<220> FEATURE:
<221> NAME/KEY: misc_feature
<222> LOCATION: (40)..(47)
<223> OTHER INFORMATION: Barcode-1
<220> FEATURE:
<221> NAME/KEY: misc_feature
<222> LOCATION: (48)..(55)
<223> OTHER INFORMATION: Anchor-2
<220> FEATURE:
<221> NAME/KEY: misc_feature
<222> LOCATION: (56)..(63)
<223> OTHER INFORMATION: Barcode-2
<220> FEATURE:
<221> NAME/KEY: misc_feature
<222> LOCATION: (64)..(71)
<223> OTHER INFORMATION: Anchor-3
<220> FEATURE:
<221> NAME/KEY: misc_feature
```

<222> LOCATION: (72)..(79)
<223> OTHER INFORMATION: Variable Barcode-3
<220> FEATURE:
<221> NAME/KEY: misc_feature
<222> LOCATION: (80)..(87)
<223> OTHER INFORMATION: Anchor-4
<220> FEATURE:
<221> NAME/KEY: misc_feature
<222> LOCATION: (88)..(100)
<223> OTHER INFORMATION: N-domain
<220> FEATURE:
<221> NAME/KEY: misc_feature
<222> LOCATION: (101)..(125)
<223> OTHER INFORMATION: poly-T domain (variable length)

<400> SEQUENCE: 40
tattaattaa tatuaagcag tggtatcaac gcagagtacc cattgaagat cgatggagtg        60
gatcatcgat cgattggttc tcacgtannn nnnnnnnnnv tttttttttt tttttttttt       120
ttttt                                                                   125

<210> SEQ ID NO 41
<211> LENGTH: 114
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Loading sequence
<220> FEATURE:
<221> NAME/KEY: misc_feature
<222> LOCATION: (2)..(28)
<223> OTHER INFORMATION: 27-mer Anchor-1
<220> FEATURE:
<221> NAME/KEY: misc_feature
<222> LOCATION: (14)..(14)
<223> OTHER INFORMATION: deoxyribouridine
<220> FEATURE:
<221> NAME/KEY: misc_feature
<222> LOCATION: (29)..(36)
<223> OTHER INFORMATION: Barcode-1
<220> FEATURE:
<221> NAME/KEY: misc_feature
<222> LOCATION: (37)..(44)
<223> OTHER INFORMATION: Anchor-2
<220> FEATURE:
<221> NAME/KEY: misc_feature
<222> LOCATION: (45)..(52)
<223> OTHER INFORMATION: Barcode-2
<220> FEATURE:
<221> NAME/KEY: misc_feature
<222> LOCATION: (53)..(60)
<223> OTHER INFORMATION: Anchor-3
<220> FEATURE:
<221> NAME/KEY: misc_feature
<222> LOCATION: (61)..(68)
<223> OTHER INFORMATION: Barcode-3
<220> FEATURE:
<221> NAME/KEY: misc_feature
<222> LOCATION: (69)..(76)
<223> OTHER INFORMATION: Anchor-4
<220> FEATURE:
<221> NAME/KEY: misc_feature
<222> LOCATION: (77)..(89)
<223> OTHER INFORMATION: N-domain
<220> FEATURE:
<221> NAME/KEY: misc_feature -continued

```
<222> LOCATION: (90)..(114)
<223> OTHER INFORMATION: poly-T domain (variable length)

<400> SEQUENCE: 41
tttttttaag caguggtatc caacgcagcc attgaagatc gatggagtgg atcatcgatc      60
gattggttct cacgtannnn nnnnnnnnvt tttttttttt tttttttttt tttt          114
```

METHODS FOR PRODUCTION AND QUANTIFICATION OF UNIQUE MOLECULAR IDENTIFIER-LABELED BEADS

CROSS REFERENCE TO RELATED APPLICATIONS

This application claims priority to U.S. Provisional Patent Application No. 63/137,264, filed on Jan. 14, 2021, which is incorporated by reference herein in its entirety.

REFERENCE TO SEQUENCE LISTING

This application is filed with a Computer Readable Form of a Sequence Listing in accordance with 37 C.F.R. § 1.821(c). The text file submitted, "013670-9061-US02_sequence_listing_4 Jan. 2022_ST25," was created on Jan. 4, 2022, contains 41 sequences, has a file size of 14.3 Kbytes, and is hereby incorporated by reference in its entirety.

TECHNICAL FIELD

Described herein are compositions and methods for the production and quantification of barcoded or unique molecular identifier (UMI)-labeled substrates. In one aspect, the substrate is a bead comprising a template oligonucleotide that is elongated by successive extension reactions to provide a bead with an oligonucleotide comprising a plurality of barcodes and conserved anchor regions. Methods are also described for quantifying the amount of template oligonucleotide loaded onto the substrate and the products of the extension reaction after each round and after the final extension.

BACKGROUND

Identifying transcriptional activity of individual cells is a current focus of many laboratories. A recently developed method for quantification of the transcriptional activity in specific cells involves the creation of barcoded or Unique Molecular Identifier (UMI)-labeled beads for RNA capture and sequencing. Generation and quantification of these is not a simple matter, however. Each bead has between 1 to 6 fmol of DNA attached, each of which possess only one barcode that is unique to that bead. As these barcodes are defined, not random, and unique (or functionally close to it) for each bead, synthesis of these barcodes is a difficult process. The sequences cannot be randomly attached to the beads because this results in a random assortment of barcodes on the surface of each bead.

Barcoded beads may therefore be made by sequentially building the sequences on the beads. This may be done several ways, including successive ligation of the desired sequences, or extension of the desired sequences across small antisense templates. Of these methods, the extension technique is superior, because it is often difficult to obtain greater than 50% ligation efficiency onto a sequence. The multiple required ligations would be multiplicative in their loss of the final obtained product, making the ligation method less desirable.

After synthesis, use of these beads in downstream techniques requires placement of each barcode labeled bead into a microwell that contains a single cell. Each well only contains one bead, and the barcode is specific for that particular cell. Extraction of the mRNA from the cell permits capturing the poly-A tail on the end of the barcoded oligonucleotide. A reverse transcriptase enzyme then can use the 3'-terminus of the barcoded oligonucleotide to copy the captured mRNA sequence. Cleavage of the resulting sequence from the bead allows for pooled next-generation sequencing of the resulting products with barcodes that identify the individual cell.

U.S. Patent Publication No. US 20180071705 A1 and Zilionis et al., "Single-cell barcoding and sequencing using droplet microfluidics," Nature Protocols 12: 44-73 (2017) describe methods for analyzing RNA sequences and transcriptional activity.

What is needed is a method that permits the synthesis of substrate-bound barcoded or unique molecular identifier (UMI)-labeled sequences for mRNA capture and quantitation of the initial substrate-loaded oligonucleotides or the resulting unique molecular identifier (UMI)-labeled extended products.

SUMMARY

One embodiment described herein is a method for preparing a unique molecular labeled substrate, the method comprising: (a) providing a substrate comprising one or more oligonucleotide templates attached to the substrate; (b) adding a primer template partially complementary to the one or more oligonucleotide templates; (c) adding reagents sufficient to perform an extension reaction; (d) incubating the extension reaction for a period of time sufficient to produce an extension product; (e) purifying the substrate comprising the extension product; (f) repeating steps (b) to (e) at least two additional times using additional primer templates partially complementary to the extended product from each subsequent round; (g) purifying the substrate comprising the final extension product using the same process as in step (e); and (h) optionally, quantitating the amount of the oligonucleotide templates attached to the substrate, the amount of extension product attached to the substrate at each round, or the amount of the final extension product attached to the substrate. In one aspect, a plurality of reactions is performed simultaneously using different primer templates partially complementary to the one or more oligonucleotide templates in step (b) and the additional primer templates partially complementary to the extended product from each subsequent round in step (f). In another aspect, at least 2, 8, 12, 16, 24, 48, 96, 192, 384, 768, 1536, or more reactions are performed simultaneously. In one aspect, the one or more oligonucleotide templates in step (a) comprises a conserved anchor sequence. In another aspect, the one or more oligonucleotide templates in step (a) comprises at least one deoxyuridine nucleotide.

In another aspect, the one or more oligonucleotide templates in step (a) comprise a single stranded oligonucleotide have a structure comprising: Substrate-Template-$N_{20-50}$-Anchor-$N_{4-20}$, wherein: Substrate is an inert substrate; Template-$N_{20-50}$ is a template sequence of 20 to 50 nucleotides optionally comprising at least one deoxyuridine nucleotide; and Anchor-$N_{4-20}$ is an anchor sequence of 4 to 20 nucleotides.

In another aspect, the one or more oligonucleotide templates in step (a) comprise a single stranded oligonucleotide have a structure comprising: Substrate-Template-$N_{20-50}$-Anchor-$N_{8-20}$, wherein: Substrate is an inert substrate; Template-$N_{20-50}$ is a template sequence of 20 to 50 nucleotides optionally comprising at least one deoxyuridine nucleotide; and Anchor-$N_{8-20}$ is an anchor sequence of 8 to 20 nucleotides.

In one aspect, the primer template partially complementary to the one or more oligonucleotide templates in step (b) and the additional primer templates partially complementary to the extended product from each subsequent round in step (f) each comprise one or more unique barcodes and one or more conserved anchor sequences.

In another aspect, the primer template partially complementary to the one or more oligonucleotide templates in step (b) and the additional primer templates partially complementary to the extended product from each subsequent round in step (f) comprise a single stranded oligonucleotide having a structure comprising: 5'-Antisense-$N_{8-20}$-Barcode-$N_{8-20}$-Anchor-$N_{4-20}$-x-3', wherein: Antisense-$N_{8-20}$ is an antisense sequence of 8 to 20 nucleotides complementary to an anchor sequence of the oligonucleotide template or the extended product; Barcode-$N_{8-20}$ is a barcode region of 8 to 20 nucleotides; Anchor-$N_{4-20}$ is an anchor sequence of 4 to 20 nucleotides; and -x is a 3'-blocking moiety to prevent extension from the 3'-terminus of the primer template.

In another aspect, the primer template partially complementary to the one or more oligonucleotide templates in step (b) and the additional primer templates partially complementary to the extended product from each subsequent round in step (f) comprise a single stranded oligonucleotide having a structure comprising: 5'-Antisense-$N_{8-20}$-Barcode-$N_{8-20}$-Anchor-$N_{8-20}$-x-3', wherein: Antisense-$N_{8-20}$ is an antisense sequence of 8 to 20 nucleotides complementary to an anchor sequence of the oligonucleotide template or the extended product; Barcode-$N_{8-20}$ is a barcode region of 8 to 20 nucleotides; Anchor-$N_{8-20}$ is an anchor sequence of 8 to 20 nucleotides; and -x is a 3'-blocking moiety to prevent extension from the 3'-terminus of the primer template.

In another aspect, the 3'-blocking moiety comprises 3'-TEG (triethylene glycol), 3'-SpC3 (1,3-propanediol), 3'-Sp18 (hexaethylene glycol), 3'-amino, 3'-phosphate, 3'-biotin, 3'-1',2'-dideoxyribose, 3'-dideoxycytidine, or 3'-inverted deoxythymidine.

In one aspect, the primer template for the final primer extension reaction in step (f) comprises a poly $A_{10-30}$ tail. In another aspect, the primer template for the final primer extension reaction in step (f) comprises a poly $N_{8-20}$ region.

In another aspect, the primer template for the final primer extension reaction in step (f) has a structure comprising: 5'-$A_{10-30}$-B-$N_{8-20}$-Anchor-$N_{4-20}$-x-3', wherein: $A_{10-30}$ is a sequence of 10 to 30 deoxyadenosine residues; B is a single deoxyguanosine, deoxycytidine, or deoxythymidine nucleotide; $N_{8-20}$ is a sequence of any 8 to 20 nucleotides; Anchor-$N_{8-20}$ is an anchor sequence of 4 to 20 nucleotides; and -x is a 3'-blocking moiety to prevent extension from the 3'-terminus of the primer template.

In another aspect, the primer template for the final primer extension reaction in step (f) has a structure comprising: 5'-$A_{10-30}$-B-$N_{8-20}$-Anchor-$N_{8-20}$-x-3', wherein: $A_{10-30}$ is a sequence of 10 to 30 deoxyadenosine residues; B is a single deoxyguanosine, deoxycytidine, or deoxythymidine nucleotide; $N_{8-20}$ is a sequence of any 8 to 20 nucleotides; Anchor-$N_{8-20}$ is an anchor sequence of 8 to 20 nucleotides; and -x is a 3'-blocking moiety to prevent extension from the 3'-terminus of the primer template.

In one aspect, the substrate is a bead or a derivatized bead, derivatized glass slide, or derivatized polymer. In another aspect, the derivatization comprises hydroxyl, carboxyl, amine, aldehyde, or sulfate moieties for coupling with nucleic acids or modified nucleic acids. In one aspect, the modified nucleic acid comprises an amino-terminated oligonucleotide. In another aspect, the derivatized bead comprises natural or synthetic polymers or hydrogels, organic or inorganic particles, glass, ceramic, metal, paramagnetic particles, or combinations thereof. In another aspect, the derivatized bead comprises poly(styrene-divinylbenzene) derivatized with hydroxyl moieties.

In another aspect, the substrate comprising one or more oligonucleotide templates has a concentration in the reaction of 10-40 mg/mL. In another aspect, the reagents sufficient to perform an extension reaction comprise: a buffered solution, deoxyribonucleotide triphosphates (dNTPs), a DNA polymerase, and optionally, a pyrophosphatase. In another aspect, the DNA polymerase is *E. coli* DNA polymerase Klenow fragment (Exo⁻). In another aspect, the DNA polymerase is provided at a ratio of 1-10 U per nmol of oligonucleotide template. In another aspect, the optional pyrophosphatase is provided at a ratio of 1 U pyrophosphatase per nmol of oligonucleotide template. In another aspect, the period of time comprises about 30 min to about 20 hours at a temperature of about 25° C. to about 37° C. with rotation at 10-20 rpm. In another aspect, the purification in step (e) comprises combining the substrates comprising the extension products together, washing the combination with hot water or buffer, and collecting the substrate comprising the primer extension product by centrifugation. In another aspect, the purification step is performed at least 3 times. In another aspect, following the purification, the substrates comprising the extension products are diluted and redistributed into individual reactions.

In one aspect, step (f) repeats steps (b) to (e) at least 3 to 100 times; each time using additional primer templates partially complementary to the extended product from each subsequent round. In another aspect, wherein step (f) repeats steps (b) to (e) at least 3 times, 4 times, 5, times, 6 times, 7 times, 8 times, 9 times, 10 times, 20 times, 50 times, 100 times, or even more; each time using additional primer templates partially complementary to the extended product from each subsequent round.

In one aspect, the quantitating the amount of the oligonucleotide templates attached to the substrate, the amount of extension product attached to the substrate at each round, or the amount of the final extension product attached to the substrate comprises one or more of: calculating the concentration of the substrate comprising an oligonucleotide template, extension product, or final extension product in solution by diluting a solution of the substrate; counting the number of substrates; applying a dilution factor; and obtaining a concentration of the substrate in solution; or cleaving the oligonucleotide templates attached to the substrate, the amount of extension product attached to the substrate at each round, or the amount of the final extension product attached to the substrate with one or more enzymes that specifically cleave the phosphodiester linkage at deoxyuridine nucleotides; and quantifying the amount of oligonucleotide templates attached to the substrate, the amount of extension product attached to the substrate at each round, or the amount of the final extension product attached to the substrate; or diluting the substrate comprising the oligonucleotide template, the extension products after a round, or the final extension product; preparing a serial dilution using control templates; adding and annealing a fluorescently quenched probe oligonucleotide to the oligonucleotide template, the extension product, the final extension product, or the serially diluted control templates to obtain fluorescently labeled double stranded sequences; measuring the fluorescence signal of the fluorescently labeled double stranded sequences; preparing a standard curve of the fluorescence signal of the control templates; and using the standard curve and the fluorescence signal of the of the oligonucleotide template, the extension product, or the final extension product to quantitate the amount (mass or moles) of the oligonucleotide template, the extension product, or the final extension product; or a combination thereof. In another aspect, the one or more enzymes in step (b) comprises a mixture of uracil DNA glycosylase and DNA glycosylase-lyase Endonuclease VIII (e.g., USER™, Uracil-Specific Excision Reagent, New England BioLabs).

Another embodiment described herein is a unique molecular labeled substrate produced by the method described herein.

Another embodiment described herein is a unique molecular labeled sequence produced by the method described herein, wherein the sequence has the structure: Template-$N_{20-50}$-Anchor-1-$N_{4-20}$-Barcode-1-$N_{8-20}$-Anchor-2-$N_{4-20}$-Barcode-2-$N_{8-20}$-Anchor-3-$N_{4-20}$-Barcode-3-$N_{8-20}$-Anchor-4-$N_{4-20}$-$N_{8-20}$-V-$T_{10-30}$, wherein: Template-$N_{20-50}$ is a template sequence of 20 to 50 nucleotides, optionally comprising at least one deoxyuridine nucleotide; Anchors-1-4-$N_{4-20}$ are anchor sequences of 4 to 20 nucleotides; Barcodes-1-4-$N_{8-20}$ are barcode regions of 8 to 20 nucleotides; $N_{8-20}$ is a sequence of any 8 to 20 nucleotides; V is a single deoxyguanosine, deoxycytidine, or deoxyadenine nucleotide; and $T_{10-30}$ is a sequence of 10 to 30 deoxythymidine residues.

Another embodiment described herein is a template oligonucleotide attached to a substrate comprising a single stranded oligonucleotide have a structure comprising: Substrate-Template-$N_{20-50}$-Anchor-$N_{4-20}$, wherein: Substrate is an inert substrate; Template-$N_{20-50}$ is a template sequence of 20 to 50 nucleotides, optionally comprising at least one deoxyuridine nucleotide; and Anchor-$N_{4-20}$ is an anchor sequence of 4 to 20 nucleotides.

Another embodiment described herein is a primer extension template comprising a single stranded oligonucleotide have a structure comprising: 5'-Antisense-$N_{8-20}$-Barcode-$N_{8-20}$-Anchor-$N_{4-20}$-x-3', wherein: Antisense-$N_{8-20}$ is an antisense sequence of 8 to 20 nucleotides complementary to an anchor sequence of the oligonucleotide template or the extended product; Barcode-$N_{8-20}$ is a barcode region of 8 to 20 nucleotides; Anchor-$N_{4-20}$ is an anchor sequence of 4 to 20 nucleotides; and -x is a 3'-blocking moiety to prevent extension from the 3'-terminus of the primer template.

Another embodiment described herein is a primer extension template comprising a single stranded oligonucleotide have a structure comprising: 5'-$A_{10-30}$-B-$N_{8-20}$-Anchor-$N_{4-20}$-x-3', wherein: $A_{10-30}$ is a sequence of 10 to 30 deoxyadenosine residues; B is a single deoxyguanosine, deoxycytidine, or deoxythymidine nucleotide; $N_{8-20}$ is a sequence of any 8 to 20 nucleotides; Anchor $N_{4-20}$ is an anchor sequence of 4 to 20 nucleotides; and -x is a 3'-blocking moiety to prevent extension from the 3'-terminus of the primer template.

Another embodiment described herein is a means or method for preparing a unique molecular labeled bead, the method or means comprising: (a) providing a bead comprising one or more oligonucleotide templates comprising a conserved anchor sequence and at least one deoxyuridine nucleotide; (b) adding a primer template partially complementary to the one or more oligonucleotide templates and comprising one or more unique barcodes, one or more conserved anchor sequences, and a 3'-blocking moiety; (c) adding a buffered solution, deoxyribonucleotide triphosphates (dNTPs), DNA polymerase Klenow fragment, and optionally, a pyrophosphatase sufficient to perform an extension reaction; (d) incubating the extension reaction for about 30 min to about 20 hours at a temperature of about 25° C. to about 37° C. with rotation at 10-20 rpm to produce an extension product; (e) purifying the bead comprising the extension product by combining the substrates comprising the extension products together, washing the combination with hot water or buffer, and collecting the substrate comprising the extension product by centrifugation, repeating the washing centrifugation step at least three times, and diluting and redistributing the extension products into individual reactions; (f) repeating steps (b) to (e) at least 3 to 100 additional times using additional primer templates partially complementary to the extended product from each prior round; (g) purifying the substrate comprising a final extended product using the same process as in step (e); and (h) optionally, quantitating the amount of the oligonucleotide templates attached to the substrate, the amount of extension product attached to the substrate at each round, or the amount of the final extension product attached to the substrate comprises; wherein: a plurality of reactions is performed simultaneously using different primer templates partially complementary to the one or more oligonucleotide templates in step (b) and the additional primer templates partially complementary to the extended product from each subsequent round in step (f); the one or more oligonucleotide templates in step (a) comprise a single stranded oligonucleotide have a structure comprising: Bead-Template-$N_{20-50}$-Anchor-$N_{4-20}$, wherein: bead is an inert bead; Template $N_{20-50}$ is a template sequence of 20 to 50 nucleotides optionally comprising at least one deoxyuridine nucleotide; and Anchor-$N_{4-20}$ is an anchor sequence of 4 to 20 nucleotides; the primer template partially complementary to the one or more oligonucleotide templates in step (b) and the additional primer templates partially complementary to the extended product from each subsequent round in step (f) have a structure comprising: 5'-Antisense-$N_{8-20}$-Barcode-$N_{8-20}$-Anchor-$N_{4-20}$-x-3', wherein: Antisense-$N_{8-20}$ is an antisense sequence of 8 to 20 nucleotides complementary to an anchor sequence of the oligonucleotide template or the extended product; Barcode-$N_{8-20}$ is a barcode region of 8 to 20 nucleotides; Anchor-$N_{4-20}$ is an anchor sequence of 4 to 20 nucleotides; and -x is a 3'-blocking moiety to prevent extension from the 3'-terminus of the primer template; and the primer template for the final primer extension reaction in step (f) has a structure comprising: 5'-$A_{10-30}$-B-$N_{8-20}$-Anchor-$N_{4-20}$-x-3', wherein: $A_{10-30}$ is a sequence of 10 to 30 deoxyadenosine residues; B is a single deoxyguanosine, deoxycytidine, or deoxythymidine nucleotide; $N_{8-20}$ is a sequence of any 8 to 20 nucleotides; Anchor-$N_{4-20}$ is an anchor sequence of 4 to 20 nucleotides; and -x is a 3'-blocking moiety to prevent extension from the 3'-terminus of the primer template.

In one aspect, the quantitating the amount of the oligonucleotide templates attached to the substrate, the amount of extension product attached to the substrate at each round, or the amount of the final extension product attached to the substrate comprises one or more of: calculating the concentration of the substrate comprising an oligonucleotide template, extension product, or final extension product in solution by diluting a solution of the substrate; counting the number of substrates; applying a dilution factor; and obtaining a concentration of the substrate in solution; or cleaving the oligonucleotide templates attached to the substrate, the amount of extension product attached to the substrate at each round, or the amount of the final extension product attached to the substrate with one or more enzymes that specifically cleave the phosphodiester linkage at deoxyuridine nucleotides; and quantifying the amount of oligonucleotide templates attached to the substrate, the amount of extension product attached to the substrate at each round, or the amount of the final extension product attached to the substrate; or diluting the substrate comprising the oligonucleotide template, the extension products after a round, or the final extension product; preparing a serial dilution using control templates; adding and annealing a fluorescently quenched probe oligonucleotide to the oligonucleotide template, the extension product, the final extension product, or the serially diluted control templates to obtain fluorescently labeled double stranded sequences; measuring the fluorescence signal of the fluorescently labeled double stranded sequences; preparing a standard curve of the fluorescence signal of the control templates; and using the standard curve and the fluorescence signal of the of the oligonucleotide template, the extension product, or the final extension product to quantitate the amount (mass or moles) of the oligonucleotide template, the extension product, or the final extension product; or a combination thereof.

Another embodiment described herein is method for capturing and analyzing mRNA, the method comprising: (a) synthesizing a substrate bound unique molecular labeled capture oligonucleotide as described herein; (b) obtaining mRNA from a cell; (c) contacting mRNA with the substrate bound unique molecular labeled capture oligonucleotide; (d) reverse transcribing the mRNA; (e) optionally amplifying the reverse transcribed mRNA; (f) analyzing the sequence of the reverse transcribed mRNA; and (g) identifying or cross-referencing the cell associated with the mRNA using the sequence and unique molecular label.

Another embodiment described herein is the use of the methods, means, or compositions described herein for the capture and analysis of mRNA.

DESCRIPTION OF THE DRAWINGS

FIG. 2C shows an exemplary primer extension campaign using an exemplary template oligonucleotide attached to a bead (SEQ ID NO: 33) and the successive primer extension steps using Primers 1, 2, 3, and 4 (SEQ ID NO: 1, 11, 21, and 31, respectively). The bold regions on the primer indicate regions complementary to the anchor sequence; the underlined regions on the primer indicate regions that are antisense to the successive anchor region. The bold and underlined sequence on the template oligonucleotide indicate the nucleotides that are added during the primer extension reaction. The final product shown is SEQ ID NO:39.

DETAILED DESCRIPTION

Figure 1:
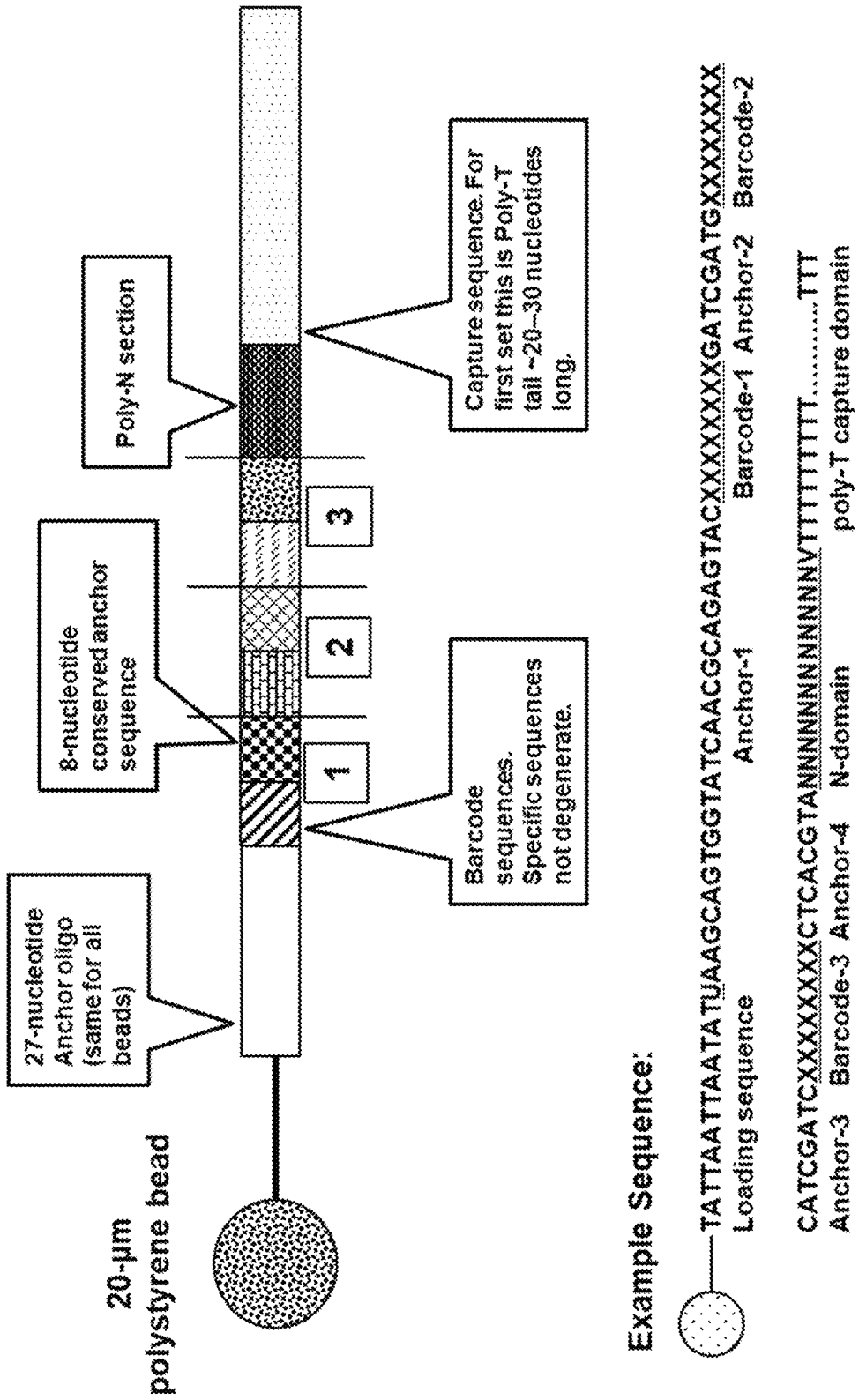
FIG. 1 shows an exemplary sequence design attached to a bead. Although many different sequences and sequence lengths can be utilized, in the example shown, a 27-mer anchor oligonucleotide is attached at the 5'-terminus to the bead and contains alternating barcodes and conserved anchor sequences (shown in regions 1, 2, and 3) as well as a poly-N Unique Molecular Identifier (UMI) region and a poly-T mRNA capture sequence. In this example, the capture sequence is shown as a poly-T, however this can be any sequence of interest. Note that all of the barcode sequences will be identical on each individual bead, but different among each bead.

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Preferred methods and materials are described below, although methods and materials similar or equivalent to those described herein can be used in practice or testing of the present invention.

As used herein, the terms "amino acid," "nucleotide," "polypeptide," "polynucleotide," and "vector" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The disclosure also contemplates other embodiments "comprising," "consisting of," and "consisting essentially of," the embodiments, aspects, or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to +10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to +10% of any value within the range or within 3 or more standard deviations, including the end points.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the phrase "an effective amount" of a compound described herein refers to an amount of the compound described herein that will elicit the biological response, for example, reduction or inhibition of an enzyme or a protein activity, or ameliorate symptoms, alleviate conditions, slow or delay disease progression, or prevent a disease, etc.

As used herein, the terms "inhibit," "inhibition," or "inhibiting" refer to the reduction or suppression of a given condition, symptom, or disorder, or disease, or a significant decrease in the baseline activity of a biological activity or process.

As used herein, the term "substrate" refers to any substrate suitable for coupling one or more oligonucleotides to the surface thereof. In one aspect, the substrate is a bead, derivatized bead, derivatized glass slide, or derivatized polymer. In another aspect, the substrate is derivatized for coupling the oligonucleotide. The derivatization can comprise hydroxyl, carboxyl, amine, aldehyde, or sulfate moieties for coupling with nucleic acids or modified nucleic acids.

As used herein, the term "antisense" refers to a region of an oligonucleotide that is complementary to another oligonucleotide. The antisense sequence can be any length, including 4-50 nucleotides, 4-20 nucleotides, 8-20 nucleotides, or any nucleotide lengths within the specified ranges. In one aspect the antisense region is specified as Antisense-$N_{X-Y}$, where N is any nucleotide and X and Y are the numbers of nucleotides. For example, "Antisense $N_{8-20}$" refers to an 8 to 20 nucleotide region of an oligonucleotide that is complementary to another oligonucleotide.

As used herein, the term "barcode" refers to a unique sequence region of an oligonucleotide that can be used to identify, track, or cross-reference the oligonucleotide sequence to a specific cell, well in a microtiter or culture plate, or other application. The barcode can be any length capable of being a unique identifier in the particular system. The barcode sequence can be any length, including 4-50 nucleotides, 4-20 nucleotides, 8-20 nucleotides, or any nucleotide lengths within the specified ranges. In one aspect the barcode region is specified as Barcode-$N_{X-Y}$, where N is any nucleotide and X and Y are the numbers of nucleotides. For example, "Barcode $N_{8-20}$" refers to an 8 to 20 nucleotide barcode region of an oligonucleotide that can be used to for identification or tracking. In one aspect the barcode is a Unique Molecular Identifier (UMI). UMIs are a type of molecular barcoding that provides error correction and increased accuracy during sequencing. UMI molecular barcodes are short, unique sequences used to tag each molecule in a sample library. UMIs are used for a wide range of sequencing applications, many around PCR duplicates in DNA and cDNA. UMI deduplication is useful for RNA-seq gene expression analysis and other quantitative sequencing methods.

As used herein, the term "anchor" refers to a conserved sequence region (i.e., a common or complementary sequence among a group of oligonucleotide primers or sequences) of an oligonucleotide that can be the target for the binding of another primer or oligonucleotide in an extension reaction. The anchor sequence can be any length, including 4-50 nucleotides, 4-20 nucleotides, 8-20 nucleotides, or any nucleotide lengths within the specified ranges. In one aspect the anchor region is specified as Anchor-$N_{X-Y}$, where N is any nucleotide and X and Y are the numbers of nucleotides. For example, "Anchor-$N_{4-20}$" refers to a 4 to 20 nucleotide region of an oligonucleotide that can serve as a complementary sequence for the binding of a primer in a (often subsequent) primer extension reaction. In one aspect, the anchor region is Anchor-$N_{4-20}$. In another aspect, the anchor region is Anchor-$N_{8-20}$.

As used herein, the primers termed "primer templates partially complementary to the extended product from each subsequent round," "additional primer templates partially complementary to the extended product from each subsequent round" or "primer template for the final primer extension reaction" are complementary to the anchor sequence of an "oligonucleotide template" or primer template from a prior extension reaction.

As used herein, the term "oligonucleotide template(s)" refers to the oligonucleotide that is coupled to the substrate and acts as a template for the first extension reaction. In one aspect, the oligonucleotide template comprises a conserved anchor sequence. In another aspect, the oligonucleotide template comprises at least one deoxyuridine nucleotide. In another aspect, the oligonucleotide template comprise a single stranded oligonucleotide have a structure comprising: Substrate-Template-$N_{20-50}$-Anchor-$N_{4-20}$, wherein: Substrate is an inert substrate; Template-$N_{20-50}$ is a template sequence of 20 to 50 nucleotides, optionally comprising at least one deoxyuridine nucleotide; and Anchor-$N_{4-20}$ is an anchor sequence of 4 to 20 nucleotides. In one aspect, the anchor sequence is Anchor-$N_{8-20}$, which is an Anchor sequence of 8 to 20 nucleotides.

As used herein, the terms "primer template partially complementary to the one or more oligonucleotide templates" or "additional primer templates partially complementary to the extended product from each subsequent round" refer to primer templates capable of hybridizing to the conserved anchor sequence present on the oligonucleotide templates or in the primer template from the preceding extension step. In one aspect, primer templates comprise one or more unique barcodes and one or more conserved anchor sequences. In another aspect, the primer templates comprise a single stranded oligonucleotide having a structure comprising: 5'-Antisense-$N_{8-20}$-Barcode-$N_{8-20}$-Anchor-$N_{4-20}$-x-3', wherein: Antisense-$N_{8-20}$ is an antisense sequence of 8 to 20 nucleotides complementary to an anchor sequence of the oligonucleotide template or the extended product; Barcode-$N_{8-20}$ is a barcode region of 8 to 20 nucleotides; Anchor-$N_{4-20}$ is an anchor sequence of 4 to 20 nucleotides; and -x is a 3'-blocking moiety to prevent extension from the 3'-terminus of the primer template. In one aspect, the anchor sequence is: Anchor-$N_{8-20}$, which is an Anchor sequence of 8 to 20 nucleotides. In one aspect, the 3'-blocking moiety comprises 3'-TEG (triethylene glycol), 3'-SpC3 (1,3-propanediol), 3'-Sp18 (hexaethylene glycol), 3'-amino, 3'-phosphate, 3'-biotin, 3'-1',2'-dideoxyribose, 3'-dideoxycytidine, or 3'-inverted deoxythymidine.

As used herein, the term "primer template for the final primer extension reaction" refers to the primer template used in the last extension reaction. In one aspect, the final primer template comprises a sequence complementary to a conserved anchor sequence of the penultimate extension product. In another aspect, the final primer template comprises a poly $N_{8-20}$ region. The poly N region may be of any length including 4-50 nucleotides, 4-20 nucleotides, 8-20 nucleotides, or any nucleotide lengths within the specified ranges. In one aspect the poly N region is specified as $N_{X-Y}$, where N is any nucleotide and X and Y are the numbers of nucleotides. In another aspect, the final primer template comprises a poly $A_{10-30}$ tail. The poly A tail may be of any length including 5-80 adenosines, 10-50 10-30 adenosines, 10-20 adenosines, or any adenosine lengths within the specified ranges. In one aspect the poly A tail is specified as $A_{X-Y}$, where A is an adenosine nucleotide and X and Y are the numbers of nucleotides. In another aspect, the final primer template comprises a single started oligonucleotide having a structure comprising: 5'-$A_{10-30}$-B-$N_{8-20}$-Anchor-$N_{4-20}$-x-3', wherein: $A_{10-30}$ is a sequence of 10 to 30 deoxyadenosine residues; B is a single deoxyguanosine, deoxycytidine, or deoxythymidine nucleotide; $N_{8-20}$ is a sequence of any 8 to 20 nucleotides; Anchor-$N_{4-20}$ is an anchor sequence of 4 to 20 nucleotides; and -x is a 3'-blocking moiety to prevent extension from the 3'-terminus of the primer template. In one aspect, the anchor sequence is Anchor-$N_{8-20}$, which is an Anchor sequence of 8 to 20 nucleotides.

The lengths of any of the nucleotide sequences or specific regions thereof described herein are exemplary and the lengths can be variable; the specified length can be decreased or increased relative to the exemplary ranges disclosed. From a practical and cost-effective standpoint, the desirable length of the sequence (or specific region) is typically the shortest nucleotide sequence that can effectively carry out the respective function without unnecessary length which increases complexity, synthesis costs, and reduces yields.

One embodiment described herein is a method for preparing a unique molecular labeled substrate, the method comprising: (a) providing a substrate comprising one or more oligonucleotide templates attached to the substrate; (b) adding a primer template partially complementary to the one or more oligonucleotide templates; (c) adding reagents sufficient to perform an extension reaction; (d) incubating the extension reaction for a period of time sufficient to produce an extension product; (e) purifying the substrate comprising the extension product; (f) repeating steps (b) to (e) at least two additional times using additional primer templates partially complementary to the extended product from each subsequent round; (g) purifying the substrate comprising the final extension product using the same process as in step (e); and (h) optionally, quantitating the amount of the oligonucleotide templates attached to the substrate, the amount of extension product attached to the substrate at each round, or the amount of the final extension product attached to the substrate. In one aspect, a plurality of reactions is performed simultaneously using different primer templates partially complementary to the one or more oligonucleotide templates in step (b) and the additional primer templates partially complementary to the extended product from each subsequent round in step (f). In another aspect, at least 2, 8, 12, 16, 24, 48, 96, 192, 384, 768, 1536, or more reactions are performed simultaneously. In one aspect, the one or more oligonucleotide templates in step (a) comprises a conserved anchor sequence. In another aspect, the one or more oligonucleotide templates in step (a) comprises at least one deoxyuridine nucleotide.

In another aspect, the one or more oligonucleotide templates in step (a) comprise a single stranded oligonucleotide have a structure comprising: Substrate-Template-$N_{20-50}$-Anchor-$N_{4-20}$, wherein: Substrate is an inert substrate; Template-$N_{20-50}$ is a template sequence of 20 to 50 nucleotides optionally comprising at least one deoxyuridine nucleotide; and Anchor-$N_{4-20}$ is an anchor sequence of 4 to 20 nucleotides.

In another aspect, the one or more oligonucleotide templates in step (a) comprise a single stranded oligonucleotide have a structure comprising: Substrate-Template-$N_{20-50}$-Anchor-$N_{8-20}$, wherein: Substrate is an inert substrate; Template-$N_{20-50}$ is a template sequence of 20 to 50 nucleotides optionally comprising at least one deoxyuridine nucleotide; and Anchor-$N_{8-20}$ is an anchor sequence of 8 to 20 nucleotides.

In one aspect, the primer template partially complementary to the one or more oligonucleotide templates in step (b) and the additional primer templates partially complementary to the extended product from each subsequent round in step (f) each comprise one or more unique barcodes and one or more conserved anchor sequences.

In another aspect, the primer template partially complementary to the one or more oligonucleotide templates in step (b) and the additional primer templates partially complementary to the extended product from each subsequent round in step (f) comprise a single stranded oligonucleotide having a structure comprising: 5'-Antisense-$N_{8-20}$-Barcode-$N_{8-20}$-Anchor-$N_{4-20}$-x-3', wherein: Antisense-$N_{8-20}$ is an antisense sequence of 8 to 20 nucleotides complementary to an anchor sequence of the oligonucleotide template or the extended product; Barcode-$N_{8-20}$ is a barcode region of 8 to 20 nucleotides; Anchor-$N_{4-20}$ is an anchor sequence of 4 to 20 nucleotides; and -x is a 3'-blocking moiety to prevent extension from the 3'-terminus of the primer template.

In another aspect, the primer template partially complementary to the one or more oligonucleotide templates in step (b) and the additional primer templates partially complementary to the extended product from each subsequent round in step (f) comprise a single stranded oligonucleotide having a structure comprising: 5'-Antisense-$N_{8-20}$-Barcode-$N_{8-20}$-Anchor-$N_{8-20}$-x-3', wherein: Antisense-$N_{8-20}$ is an antisense sequence of 8 to 20 nucleotides complementary to an anchor sequence of the oligonucleotide template or the extended product; Barcode-$N_{8-20}$ is a barcode region of 8 to 20 nucleotides; Anchor-$N_{8-20}$ is an anchor sequence of 8 to 20 nucleotides; and -x is a 3'-blocking moiety to prevent extension from the 3'-terminus of the primer template.

In another aspect, the 3'-blocking moiety comprises 3'-TEG (triethylene glycol), 3'-SpC3 (1,3-propanediol), 3'-Sp18 (hexaethylene glycol), 3'-amino, 3'-phosphate, 3'-biotin, 3'-1',2'-dideoxyribose, 3'-dideoxycytidine, or 3'-inverted deoxythymidine.

In one aspect, the primer template for the final primer extension reaction in step (f) comprises a poly $A_{10-30}$ tail. In another aspect, the primer template for the final primer extension reaction in step (f) comprises a poly $N_{8-20}$ region.

In another aspect, the primer template for the final primer extension reaction in step (f) has a structure comprising: 5'-$A_{10-30}$-B-$N_{8-20}$-Anchor-$N_{4-20}$-x-3', wherein: $A_{10-30}$ is a sequence of 10 to 30 deoxyadenosine residues; B is a single deoxyguanosine, deoxycytidine, or deoxythymidine nucleotide; $N_{8-20}$ is a sequence of any 8 to 20 nucleotides; Anchor-$N_{8-20}$ is an anchor sequence of 4 to 20 nucleotides; and -x is a 3'-blocking moiety to prevent extension from the 3'-terminus of the primer template.

In another aspect, the primer template for the final primer extension reaction in step (f) has a structure comprising: 5'-$A_{10-30}$-B-$N_{8-20}$-Anchor-$N_{8-20}$-x-3', wherein: $A_{10-30}$ is a sequence of 10 to 30 deoxyadenosine residues; B is a single deoxyguanosine, deoxycytidine, or deoxythymidine nucleotide; $N_{8-20}$ is a sequence of any 8 to 20 nucleotides; Anchor-$N_{8-20}$ is an anchor sequence of 8 to 20 nucleotides; and -x is a 3'-blocking moiety to prevent extension from the 3'-terminus of the primer template.

In one aspect, the substrate is a bead or a derivatized bead, derivatized glass slide, or derivatized polymer. In another aspect, the derivatization comprises hydroxyl, carboxyl, amine, aldehyde, or sulfate moieties for coupling with nucleic acids or modified nucleic acids. In one aspect, the modified nucleic acid comprises an amino-terminated oligonucleotide. In another aspect, the derivatized bead comprises natural or synthetic polymers or hydrogels, organic or inorganic particles, glass, ceramic, metal, paramagnetic particles, or combinations thereof. In another aspect, the derivatized bead comprises poly(styrene-divinylbenzene) derivatized with hydroxyl moieties.

In another aspect, the substrate comprising one or more oligonucleotide templates has a concentration in the reaction of 10-40 mg/mL. In another aspect, the reagents sufficient to perform an extension reaction comprise: a buffered solution, deoxyribonucleotide triphosphates (dNTPs), a DNA polymerase, and optionally, a pyrophosphatase. In another aspect, the DNA polymerase is *E. coli* DNA polymerase Klenow fragment (Exo-). In another aspect, the DNA polymerase is provided at a ratio of 1-10 U per nmol of oligonucleotide template. In another aspect, the optional pyrophosphatase is provided at a ratio of 1 U pyrophosphatase per nmol of oligonucleotide template. In another aspect, the period of time comprises about 30 min to about 20 hours at a temperature of about 25° C. to about 37° C. with rotation at 10-20 rpm. In another aspect, the purification in step (e) comprises combining the substrates comprising the extension products together, washing the combination with hot water or buffer, and collecting the substrate comprising the primer extension product by centrifugation. In another aspect, the purification step is performed at least 3 times. In another aspect, following the purification, the substrates comprising the extension products are diluted and redistributed into individual reactions.

In one aspect, step (f) repeats steps (b) to (e) at least 3 to 100 times; each time using additional primer templates partially complementary to the extended product from each subsequent round. In another aspect, wherein step (f) repeats steps (b) to (e) at least 3 times, 4 times, 5, times, 6 times, 7 times, 8 times, 9 times, 10 times, 20 times, 50 times, 100 times, or even more; each time using additional primer templates partially complementary to the extended product from each subsequent round.

In one aspect, the quantitating the amount of the oligonucleotide templates attached to the substrate, the amount of extension product attached to the substrate at each round, or the amount of the final extension product attached to the substrate comprises one or more of: calculating the concentration of the substrate comprising an oligonucleotide template, extension product, or final extension product in solution by diluting a solution of the substrate; counting the number of substrates; applying a dilution factor; and obtaining a concentration of the substrate in solution; or cleaving the oligonucleotide templates attached to the substrate, the amount of extension product attached to the substrate at each round, or the amount of the final extension product attached to the substrate with one or more enzymes that specifically cleave the phosphodiester linkage at deoxyuridine nucleotides; and quantifying the amount of oligonucleotide templates attached to the substrate, the amount of extension product attached to the substrate at each round, or the amount of the final extension product attached to the substrate; or diluting the substrate comprising the oligonucleotide template, the extension products after a round, or the final extension product; preparing a serial dilution using control templates; adding and annealing a fluorescently quenched probe oligonucleotide to the oligonucleotide template, the extension product, the final extension product, or the serially diluted control templates to obtain fluorescently labeled double stranded sequences; measuring the fluorescence signal of the fluorescently labeled double stranded sequences; preparing a standard curve of the fluorescence signal of the control templates; and using the standard curve and the fluorescence signal of the of the oligonucleotide template, the extension product, or the final extension product to quantitate the amount (mass or moles) of the oligonucleotide template, the extension product, or the final extension product; or a combination thereof. In another aspect, the one or more enzymes in step (b) comprises a mixture of uracil DNA glycosylase and DNA glycosylase-lyase Endonuclease VIII (e.g., USER™, Uracil-Specific Excision Reagent, New England BioLabs).

Another embodiment described herein is a unique molecular labeled substrate produced by the method described herein.

Another embodiment described herein is a unique molecular labeled sequence produced by the method described herein, wherein the sequence has the structure: Template-$N_{20-50}$-Anchor-1-$N_{4-20}$-Barcode-1-$N_{8-20}$-Anchor-2-$N_{4-20}$-Barcode-2-$N_{8-20}$-Anchor-3-$N_{4-20}$-Barcode-3-$N_{8-20}$-Anchor-4-$N_{4-20}$-$N_{8-20}$-V-$T_{10-30}$, wherein: Template-$N_{20-50}$ is a template sequence of 20 to 50 nucleotides, optionally comprising at least one deoxyuridine nucleotide; Anchors-1-4-$N_{4-20}$ are anchor sequences of 4 to 20 nucleotides; Barcodes-1-4-$N_{8-20}$ are barcode regions of 8 to 20 nucleotides; $N_{8-20}$ is a sequence of any 8 to 20 nucleotides; V is a single deoxyguanosine, deoxycytidine, or deoxyadenine nucleotide; and $T_{10-30}$ is a sequence of 10 to 30 deoxythymidine residues.

Another embodiment described herein is a template oligonucleotide attached to a substrate comprising a single stranded oligonucleotide have a structure comprising: Substrate-Template-$N_{20-50}$-Anchor-$N_{4-20}$, wherein: Substrate is an inert substrate; Template-$N_{20-50}$ is a template sequence of 20 to 50 nucleotides, optionally comprising at least one deoxyuridine nucleotide; and Anchor-$N_{4-20}$ is an anchor sequence of 4 to 20 nucleotides.

Another embodiment described herein is a primer extension template comprising a single stranded oligonucleotide have a structure comprising: 5'-Antisense-$N_{8-20}$-Barcode-$N_{8-20}$-Anchor-$N_{4-20}$-x-3', wherein: Antisense-$N_{8-20}$ is an antisense sequence of 8 to 20 nucleotides complementary to an anchor sequence of the oligonucleotide template or the extended product; Barcode-$N_{8-20}$ is a barcode region of 8 to 20 nucleotides; Anchor-$N_{4-20}$ is an anchor sequence of 4 to 20 nucleotides; and -x is a 3'-blocking moiety to prevent extension from the 3'-terminus of the primer template.

Another embodiment described herein is a primer extension template comprising a single stranded oligonucleotide have a structure comprising: 5'-$A_{10-30}$-B-$N_{8-20}$-Anchor-$N_{4-20}$-x-3', wherein: $A_{10-30}$ is a sequence of 10 to 30 deoxyadenosine residues; B is a single deoxyguanosine, deoxycytidine, or deoxythymidine nucleotide; $N_{8-20}$ is a sequence of any 8 to 20 nucleotides; Anchor $N_{4-20}$ is an anchor sequence of 4 to 20 nucleotides; and -x is a 3'-blocking moiety to prevent extension from the 3'-terminus of the primer template.

Another embodiment described herein is a means or method for preparing a unique molecular labeled bead, the method or means comprising: (a) providing a bead comprising one or more oligonucleotide templates comprising a conserved anchor sequence and at least one deoxyuridine nucleotide; (b) adding a primer template partially complementary to the one or more oligonucleotide templates and comprising one or more unique barcodes, one or more conserved anchor sequences, and a 3'-blocking moiety; (c) adding a buffered solution, deoxyribonucleotide triphosphates (dNTPs), DNA polymerase Klenow fragment, and optionally, a pyrophosphatase sufficient to perform an extension reaction; (d) incubating the extension reaction for about 30 min to about 20 hours at a temperature of about 25° C. to about 37° C. with rotation at 10-20 rpm to produce an extension product; (e) purifying the bead comprising the extension product by combining the substrates comprising the extension products together, washing the combination with hot water or buffer, and collecting the substrate comprising the extension product by centrifugation, repeating the washing centrifugation step at least three times, and diluting and redistributing the extension products into individual reactions; (f) repeating steps (b) to (e) at least 3 to 100 additional times using additional primer templates partially complementary to the extended product from each prior round; (g) purifying the substrate comprising a final extended product using the same process as in step (e); and (h) optionally, quantitating the amount of the oligonucleotide templates attached to the substrate, the amount of extension product attached to the substrate at each round, or the amount of the final extension product attached to the substrate comprises; wherein: a plurality of reactions is performed simultaneously using different primer templates partially complementary to the one or more oligonucleotide templates in step (b) and the additional primer templates partially complementary to the extended product from each subsequent round in step (f); the one or more oligonucleotide templates in step (a) comprise a single stranded oligonucleotide have a structure comprising: Bead-Template-$N_{20-50}$-Anchor-$N_{4-20}$, wherein: bead is an inert bead; Template $N_{20-50}$ is a template sequence of 20 to 50 nucleotides optionally comprising at least one deoxyuridine nucleotide; and Anchor-$N_{4-20}$ is an anchor sequence of 4 to 20 nucleotides; the primer template partially complementary to the one or more oligonucleotide templates in step (b) and the additional primer templates partially complementary to the extended product from each subsequent round in step (f) have a structure comprising: 5'-Antisense-$N_{8-20}$-Barcode-$N_{8-20}$-Anchor-$N_{4-20}$-x-3', wherein: Antisense-$N_{8-20}$ is an antisense sequence of 8 to 20 nucleotides complementary to an anchor sequence of the oligonucleotide template or the extended product; Barcode-$N_{8-20}$ is a barcode region of 8 to 20 nucleotides; Anchor-$N_{4-20}$ is an anchor sequence of 4 to 20 nucleotides; and -x is a 3'-blocking moiety to prevent extension from the 3'-terminus of the primer template; and the primer template for the final primer extension reaction in step (f) has a structure comprising: 5'-$A_{10-30}$-B-$N_{8-20}$-Anchor-$N_{4-20}$-x-3', wherein: $A_{10-30}$ is a sequence of 10 to 30 deoxyadenosine residues; B is a single deoxyguanosine, deoxycytidine, or deoxythymidine nucleotide; $N_{8-20}$ is a sequence of any 8 to 20 nucleotides; Anchor-$N_{4-20}$ is an anchor sequence of 4 to 20 nucleotides; and -x is a 3'-blocking moiety to prevent extension from the 3'-terminus of the primer template.

In one aspect, the quantitating the amount of the oligonucleotide templates attached to the substrate, the amount of extension product attached to the substrate at each round, or the amount of the final extension product attached to the substrate comprises one or more of: calculating the concentration of the substrate comprising an oligonucleotide template, extension product, or final extension product in solution by diluting a solution of the substrate; counting the number of substrates; applying a dilution factor; and obtaining a concentration of the substrate in solution; or cleaving the oligonucleotide templates attached to the substrate, the amount of extension product attached to the substrate at each round, or the amount of the final extension product attached to the substrate with one or more enzymes that specifically cleave the phosphodiester linkage at deoxyuridine nucleotides; and quantifying the amount of oligonucleotide templates attached to the substrate, the amount of extension product attached to the substrate at each round, or the amount of the final extension product attached to the substrate; or diluting the substrate comprising the oligonucleotide template, the extension products after a round, or the final extension product; preparing a serial dilution using control templates; adding and annealing a fluorescently quenched probe oligonucleotide to the oligonucleotide template, the extension product, the final extension product, or the serially diluted control templates to obtain fluorescently labeled double stranded sequences; measuring the fluorescence signal of the fluorescently labeled double stranded sequences; preparing a standard curve of the fluorescence signal of the control templates; and using the standard curve and the fluorescence signal of the of the oligonucleotide template, the extension product, or the final extension product to quantitate the amount (mass or moles) of the oligonucleotide template, the extension product, or the final extension product; or a combination thereof.

Another embodiment described herein is method for capturing and analyzing mRNA, the method comprising: (a) synthesizing a substrate bound unique molecular labeled capture oligonucleotide as described herein; (b) obtaining mRNA from a cell; (c) contacting mRNA with the substrate bound unique molecular labeled capture oligonucleotide; (d) reverse transcribing the mRNA; (e) optionally amplifying the reverse transcribed mRNA; (f) analyzing the sequence of the reverse transcribed mRNA; and (g) identifying or cross-referencing the cell associated with the mRNA using the sequence and unique molecular label.

Another embodiment described herein is the use of the methods, means, or compositions described herein for the capture and analysis of mRNA.

The polynucleotides described herein include variants that have substitutions, deletions, and/or additions that can involve one or more nucleotides. The variants can be altered in coding regions, non-coding regions, or both. Alterations in the coding regions can produce conservative or non-conservative amino acid substitutions, deletions, or additions. Especially preferred among these are silent substitutions, additions, and deletions, which do not alter the properties and activities of the binding.

Further embodiments described herein include nucleic acid molecules comprising polynucleotides having nucleotide sequences about 50%, 55%, 60%, 65%, 70%, 75%, 80%, 85%, 90%, 91%, 92%, 93%, 94%, 95%, 96%, 97%, 98%, or 99% identical, and more preferably at least about 90-99% identical to (a) nucleotide sequences, or degenerate, homologous, or codon-optimized variants thereof; or (b) nucleotide sequences capable of hybridizing to the complement of any of the nucleotide sequences in (a).

By a polynucleotide having a nucleotide sequence at least, for example, 90-99% "identical" to a reference nucleotide sequence is intended that the nucleotide sequence of the polynucleotide be identical to the reference sequence except that the polynucleotide sequence can include up to about 10 to 1 point mutations, additions, or deletions per each 100 nucleotides of the reference nucleotide sequence.

In other words, to obtain a polynucleotide having a nucleotide sequence about at least 90-99% identical to a reference nucleotide sequence, up to 10% of the nucleotides in the reference sequence can be deleted, added, or substituted, with another nucleotide, or a number of nucleotides up to 10% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence. The same is applicable to polypeptide sequences about at least 90-99% identical to a reference polypeptide sequence.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

Various embodiments and aspects of the inventions described herein are summarized by the following clauses:

Clause 1. A method for preparing a unique molecular labeled substrate, the method comprising:
  (a) providing a substrate comprising one or more oligonucleotide templates attached to the substrate;
  (b) adding a primer template partially complementary to the one or more oligonucleotide templates;
  (c) adding reagents sufficient to perform an extension reaction;
  (d) incubating the extension reaction for a period of time sufficient to produce an extension product;
  (e) purifying the substrate comprising the extension product;
  (f) repeating steps (b) to (e) at least two additional times using additional primer templates partially complementary to the extended product from each subsequent round;
  (g) purifying the substrate comprising the final extension product using the same process as in step (e); and
  (h) optionally, quantitating the amount of the oligonucleotide templates attached to the substrate, the amount of extension product attached to the substrate at each round, or the amount of the final extension product attached to the substrate.

Clause 2. The method of clause 1, wherein a plurality of reactions is performed simultaneously using different primer templates partially complementary to the one or more oligonucleotide templates in step (b) and the additional primer templates partially complementary to the extended product from each subsequent round in step (f).

Clause 3. The method of clause 2, wherein at least 2, 8, 12, 16, 24, 48, 96, 192, 384, 768, 1536, or more reactions are performed simultaneously.

Clause 4. The method of clause 1, wherein the one or more oligonucleotide templates in step (a) comprises a conserved anchor sequence.

Clause 5. The method of clause 1, wherein the one or more oligonucleotide templates in step (a) comprises at least one deoxyuridine nucleotide.

Clause 6. The method of clause 1, wherein the one or more oligonucleotide templates in step (a) comprise a single stranded oligonucleotide have a structure comprising:

Substrate-Template-$N_{20-50}$-Anchor-$N_{4-20}$, wherein:
Substrate is an inert substrate;
Template-$N_{20-50}$ is a template sequence of 20 to 50 nucleotides optionally comprising at least one deoxyuridine nucleotide; and
Anchor-$N_{4-20}$ is an anchor sequence of 4 to 20 nucleotides.

Clause 7. The method of clause 1, wherein the one or more oligonucleotide templates in step (a) comprise a single stranded oligonucleotide have a structure comprising:

Substrate-Template-$N_{20-50}$-Anchor-$N_{8-20}$, wherein:
Substrate is an inert substrate;
Template-$N_{20-50}$ is a template sequence of 20 to 50 nucleotides optionally comprising at least one deoxyuridine nucleotide; and
Anchor-$N_{8-20}$ is an anchor sequence of 8 to 20 nucleotides.

Clause 8. The method of clause 1, wherein the primer template partially complementary to the one or more oligonucleotide templates in step (b) and the additional primer templates partially complementary to the extended product from each subsequent round in step (f) each comprise one or more unique barcodes and one or more conserved anchor sequences.

Clause 9. The method of clause 1, wherein the primer template partially complementary to the one or more oligonucleotide templates in step (b) and the additional primer templates partially complementary to the extended product from each subsequent round in step (f) comprise a single stranded oligonucleotide having a structure comprising:

5'-Antisense-$N_{8-20}$-Barcode-$N_{8-20}$-Anchor-$N_{4-20}$-x-3', wherein:
Antisense-$N_{8-20}$ is an antisense sequence of 8 to 20 nucleotides complementary to an anchor sequence of the oligonucleotide template or the extended product;
Barcode-$N_{8-20}$ is a barcode region of 8 to 20 nucleotides;
Anchor-$N_{4-20}$ is an anchor sequence of 4 to 20 nucleotides; and
x is a 3'-blocking moiety to prevent extension from the 3'-terminus of the primer template.

Clause 10. The method of clause 1, wherein the primer template partially complementary to the one or more oligonucleotide templates in step (b) and the additional primer templates partially complementary to the extended product from each subsequent round in step (f) comprise a single stranded oligonucleotide having a structure comprising:

5'-Antisense-$N_{8-20}$-Barcode-$N_{8-20}$-Anchor-$N_{8-20}$-x-3', wherein:
Antisense-$N_{8-20}$ is an antisense sequence of 8 to 20 nucleotides complementary to an anchor sequence of the oligonucleotide template or the extended product;
Barcode-$N_{8-20}$ is a barcode region of 8 to 20 nucleotides;
Anchor-$N_{8-20}$ is an anchor sequence of 8 to 20 nucleotides; and
x is a 3'-blocking moiety to prevent extension from the 3'-terminus of the primer template.

Clause 11. The method of clause 9 or 10, wherein the 3'-blocking moiety comprises 3'-TEG (triethylene glycol), 3'-SpC3 (1,3-propanediol), 3'-Sp18 (hexaethylene glycol), 3'-amino, 3'-phosphate, 3'-biotin, 3'-1',2'-dideoxyribose, 3'-dideoxycytidine, or 3'-inverted deoxythymidine.

Clause 12. The method of clause 1, wherein the primer template for the final primer extension reaction in step (f) comprises a poly $A_{10-30}$ tail.

Clause 13. The method of clause 1, wherein the primer template for the final primer extension reaction in step (f) comprises a poly $N_{8-20}$ region.

Clause 14. The method of clause 1, wherein the primer template for the final primer extension reaction in step (f) comprising a single stranded oligonucleotide having a structure comprising:

5'-$A_{10-30}$-B-$N_{8-20}$-Anchor $N_{4-20}$-x-3', wherein:
$A_{10-30}$ is a sequence of 10 to 30 deoxyadenosine residues;
B is a single deoxyguanosine, deoxycytidine, or deoxythymidine nucleotide;
$N_{8-20}$ is a sequence of any 8 to 20 nucleotides;
Anchor $N_{4-20}$ is an anchor sequence of 4 to 20 nucleotides; and
x is a 3'-blocking moiety to prevent extension from the 3'-terminus of the primer template.

Clause 15. The method of clause 1, wherein the primer template for the final primer extension reaction in step (f) comprising a single stranded oligonucleotide having a structure comprising:

5'-$A_{10-30}$-B-$N_{8-20}$-Anchor $N_{8-20}$-x-3', wherein:
$A_{10-30}$ is a sequence of 10 to 30 deoxyadenosine residues;
B is a single deoxyguanosine, deoxycytidine, or deoxythymidine nucleotide;
$N_{8-20}$ is a sequence of any 8 to 20 nucleotides;
Anchor $N_{8-20}$ is an anchor sequence of 8 to 20 nucleotides; and
x is a 3'-blocking moiety to prevent extension from the 3'-terminus of the primer template.

Clause 16. The method of clause 1, wherein the substrate is a bead, derivatized bead, derivatized glass slide, or derivatized polymer.

Clause 17. The method of clause 16, wherein the derivatization comprises hydroxyl, carboxyl, amine, aldehyde, or sulfate moieties for coupling with nucleic acids or modified nucleic acids.

Clause 18. The method of clause 17, wherein the modified nucleic acid comprises an amino-terminated oligonucleotide.

Clause 19. The method of clause 16, wherein the derivatized bead comprises natural or synthetic polymers or hydrogels, organic or inorganic particles, glass, ceramic, metal, paramagnetic particles, or combinations thereof.

Clause 20. The method of clause 16, wherein the derivatized bead comprises poly(styrene-divinylbenzene) derivatized with hydroxyl moieties.

Clause 21. The method of clause 1, wherein the substrate comprising one or more oligonucleotide templates has a concentration in the reaction of 10-40 mg/mL.

Clause 22. The method of clause 1, wherein the reagents sufficient to perform an extension reaction comprise: a buffered solution, deoxyribonucleotide triphosphates (dNTPs), a DNA polymerase, and optionally, a pyrophosphatase.

Clause 23. The method of clause 22, wherein the DNA polymerase is *E. coli* DNA polymerase Klenow fragment (Exo-).

Clause 24. The method of clause 22, wherein the DNA polymerase is provided at a ratio of 1-10 U per nmol of oligonucleotide template.

Clause 25. The method of clause 22, wherein the optional pyrophosphatase is provided at a ratio of 1 U pyrophosphatase per nmol of oligonucleotide template.

Clause 26. The method of clause 1, wherein the period of time comprises about 30 min to about 20 hours at a temperature of about 25° C. to about 37° C. with rotation at 10-20 rpm.

Clause 27. The method of clause 1, wherein the purification in step (e) comprises combining the substrates comprising the extension products together, washing the combination with hot water or buffer, and collecting the substrate comprising the primer extension product by centrifugation.

Clause 28. The method of clause 27, wherein the purification step is performed at least 3 times.

Clause 29. The method of clause 1, wherein following the purification in step (e), the substrates comprising the extension products are diluted and redistributed into individual reactions.

Clause 30. The method of clause 1, wherein step (f) repeats steps (b) to (e) at least 3 to 100 times; each time using additional primer templates partially complementary to the extended product from each subsequent round.

Clause 31. The method of clause 1, wherein step (f) repeats steps (b) to (e) at least 3 times, 4 times, 5, times, 6 times, 7 times, 8 times, 9 times, 10 times, 20 times, 50 times, 100 times, or even more each time using additional primer templates partially complementary to the extended product from each subsequent round.

Clause 32. The method of clause 1, wherein the quantitating the amount of the oligonucleotide templates attached to the substrate, the amount of extension product attached to the substrate at each round, or the amount of the final extension product attached to the substrate comprises one or more of:
(a) calculating the concentration of the substrate comprising an oligonucleotide template, extension product, or final extension product in solution by diluting a solution of the substrate;
counting the number of substrates;
applying a dilution factor; and
obtaining a concentration of the substrate in solution; or
(b) cleaving the oligonucleotide templates attached to the substrate, the amount of extension product attached to the substrate at each round, or the amount of the final extension product attached to the substrate with one or more enzymes that specifically cleave the phosphodiester linkage at deoxyuridine nucleotides; and quantifying the amount of oligonucleotide templates attached to the substrate, the amount of extension product attached to the substrate at each round, or the amount of the final extension product attached to the substrate; or
(c) diluting the substrate comprising the oligonucleotide template, the extension products after a round, or the final extension product;
preparing a serial dilution using control templates;
adding and annealing a fluorescently quenched probe oligonucleotide to the oligonucleotide template, the extension product, the final extension product, or the serially diluted control templates to obtain fluorescently labeled double stranded sequences;
measuring the fluorescence signal of the fluorescently labeled double stranded sequences;
preparing a standard curve of the fluorescence signal of the control templates; and
using the standard curve and the fluorescence signal of the of the oligonucleotide template, the extension product, or the final extension product to quantitate the amount (mass or moles) of the oligonucleotide template, the extension product, or the final extension product; or
a combination thereof.

Clause 33. The method of clause 32, wherein the one or more enzymes in step (b) comprises a mixture of uracil DNA glycosylase and DNA glycosylase-lyase Endonuclease VIII (e.g., USER™, Uracil-Specific Excision Reagent, New England BioLabs).

Clause 34. A unique molecular labeled sequence produced by the method of any one of clauses 1-33.

Clause 35. A unique molecular labeled sequence produced by the method of any one of clauses 1-33, wherein the sequence has the structure:

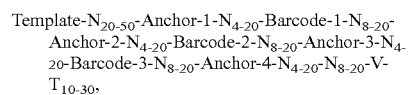

Template-$N_{20-50}$-Anchor-1-$N_{4-20}$-Barcode-1-$N_{8-20}$-Anchor-2-$N_{4-20}$-Barcode-2-$N_{8-20}$-Anchor-3-$N_{4-20}$-Barcode-3-$N_{8-20}$-Anchor-4-$N_{4-20}$-$N_{8-20}$-V-$T_{10-30}$, wherein:
Template-$N_{20-50}$ is a template sequence of 20 to 50 nucleotides, optionally comprising at least one deoxyuridine nucleotide;
Anchors-1-4-$N_{4-20}$ are anchor sequences of 4 to 20 nucleotides;
Barcodes-1-4-$N_{8-20}$ are barcode regions of 8 to 20 nucleotides;
$N_{8-20}$ is a sequence of any 8 to 20 nucleotides;
V is a single deoxyguanosine, deoxycytidine, or deoxyadenine nucleotide; and
$T_{10-30}$ is a sequence of 10 to 30 deoxythymidine residues.

Clause 36. A template oligonucleotide attached to a substrate comprising a single stranded oligonucleotide have a structure comprising:

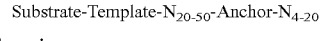

Substrate-Template-$N_{20-50}$-Anchor-$N_{4-20}$ wherein:
Substrate is an inert substrate;
Template-$N_{20-50}$ is a template sequence of 20 to 50 nucleotides, optionally comprising at least one deoxyuridine nucleotide; and
Anchor-$N_{4-20}$ is an anchor sequence of 4 to 20 nucleotides.

Clause 37. A primer extension template comprising a single stranded oligonucleotide have a structure comprising:

5'-Antisense-$N_{8-20}$-Barcode-$N_{8-20}$-Anchor-$N_{4-20}$-x-3', wherein:
Antisense-$N_{8-20}$ is an antisense sequence of 8 to 20 nucleotides complementary to an anchor sequence of the oligonucleotide template or the extended product;
Barcode-$N_{8-20}$ is a barcode region of 8 to 20 nucleotides;
Anchor-$N_{4-20}$ is an anchor sequence of 4 to 20 nucleotides; and
x is a 3'-blocking moiety to prevent extension from the 3'-terminus of the primer template.

Clause 38. A primer extension template comprising a single stranded oligonucleotide having a structure comprising:

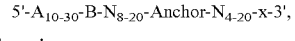

5'-$A_{10-30}$-B-$N_{8-20}$-Anchor-$N_{4-20}$-x-3', wherein:
$A_{10-30}$ is a sequence of 10 to 30 deoxyadenosine residues;
B is a single deoxyguanosine, deoxycytidine, or deoxythymidine nucleotide;
$N_{8-20}$ is a sequence of any 8 to 20 nucleotides;

Anchor-$N_{4-20}$ is an anchor sequence of 4 to 20 nucleotides; and x is a 3'-blocking moiety to prevent extension from the 3'-terminus of the primer template.

Clause 39. A means or method for preparing a unique molecular labeled bead, the method or Clause 39. means comprising:
(a) providing a bead comprising one or more oligonucleotide templates comprising a conserved anchor sequence and a deoxyuridine nucleotide;
(b) adding a primer template partially complementary to the one or more oligonucleotide templates and comprising one or more unique barcodes, one or more conserved anchor sequences, and a 3'-blocking moiety;
(c) adding a buffered solution, deoxyribonucleotide triphosphates (dNTPs), DNA polymerase Klenow fragment, and optionally, a pyrophosphatase sufficient to perform an extension reaction;
(d) incubating the extension reaction for about 30 min to about 20 hours at a temperature of about 25° C. to about 37° C. with rotation at 10-20 rpm to produce an extension product;
(e) purifying the bead comprising the extension product by combining the substrates comprising the extension products together, washing the combination with hot water or buffer, and collecting the substrate comprising the extension product by centrifugation, repeating the washing centrifugation step at least three times, and diluting and redistributing the extension products into individual reactions;
(f) repeating steps (b) to (e) at least 3 to 100 additional times using additional primer templates partially complementary to the extended product from each prior round;
(g) purifying the substrate comprising a final extended product using the same process as in step (e); and
(h) optionally, quantitating the amount of the oligonucleotide templates attached to the substrate, the amount of extension product attached to the substrate at each round, or the amount of the final extension product attached to the substrate comprises;

wherein:
a plurality of reactions is performed simultaneously using different primer templates partially complementary to the one or more oligonucleotide templates in step (b) and the additional primer templates partially complementary to the extended product from each subsequent round in step (f);

the one or more oligonucleotide templates in step (a) comprise a single stranded oligonucleotide have a structure comprising:

Bead-Template-$N_{20-50}$-Anchor-$N_{4-20}$ wherein:
bead is an inert bead;
Template-$N_{20-50}$ is a template sequence of 20 to 50 nucleotides, optionally comprising at least one deoxyuridine nucleotide; and
Anchor-$N_{4-20}$ is an anchor sequence of 4 to 20 nucleotides;

the primer template partially complementary to the one or more oligonucleotide templates in step (b) and the additional primer templates partially complementary to the extended product from each subsequent round in step (f) comprise a single stranded oligonucleotide having a structure comprising:

5'-Antisense-$N_{8-20}$-Barcode-$N_{8-20}$-Anchor-$N_{4-20}$-X-3', wherein:
Antisense-$N_{8-20}$ is an antisense sequence of 8 to 20 nucleotides complementary to an anchor sequence of the oligonucleotide template or the extended product;
Barcode-$N_{8-20}$ is a barcode region of 8 to 20 nucleotides;
Anchor-$N_{4-20}$ is an anchor sequence of 4 to 20 nucleotides; and
x is a 3'-blocking moiety to prevent extension from the 3'-terminus of the primer template; and the primer template for the final primer extension reaction in step (f) has a structure comprising:

5'-$A_{10-30}$-B-$N_{8-20}$-Anchor-$N_{4-20}$-x-3', wherein:
$A_{10-30}$ is a sequence of 10 to 30 deoxyadenosine residues;
B is a single deoxyguanosine, deoxycytidine, or deoxythymidine nucleotide;
N& 20 is a sequence of any 8 to 20 nucleotides;
Anchor-$N_{4-20}$ is an anchor sequence of 4 to 20 nucleotides; and
x is a 3'-blocking moiety to prevent extension from the 3'-terminus of the primer template.

Clause 40. The method of clause 39, wherein the quantitating the amount of the oligonucleotide templates attached to the substrate, the amount of extension product attached to the substrate at each round, or the amount of the final extension product attached to the substrate comprises one or more of:
(a) calculating the concentration of the substrate comprising an oligonucleotide template, extension product, or final extension product in solution by diluting a solution of the substrate;
counting the number of substrates;
applying a dilution factor; and
obtaining a concentration of the substrate in solution;
or
(b) cleaving the oligonucleotide templates attached to the substrate, the amount of extension product attached to the substrate at each round, or the amount of the final extension product attached to the substrate with one or more enzymes that specifically cleave the phosphodiester linkage at deoxyuridine nucleotides; and quantifying the amount of oligonucleotide templates attached to the substrate, the amount of extension product attached to the substrate at each round, or the amount of the final extension product attached to the substrate;
or
(c) diluting the substrate comprising the oligonucleotide template, the extension products after a round, or the final extension product;
preparing a serial dilution using control templates;
adding and annealing a fluorescently quenched probe oligonucleotide to the oligonucleotide template, the extension product, the final extension product, or the serially diluted control templates to obtain fluorescently labeled double stranded sequences;
measuring the fluorescence signal of the fluorescently labeled double stranded sequences;
preparing a standard curve of the fluorescence signal of the control templates; and
using the standard curve and the fluorescence signal of the of the oligonucleotide template, the extension product, or the final extension product to quantitate the amount (mass or moles) of the oligonucleotide template, the extension product, or the final extension product; or a combination thereof.

Clause 41. A method for capturing and analyzing mRNA, the method comprising:
(a) synthesizing a substrate bound unique molecular labeled capture oligonucleotide as described in clauses 1-33 or 39-40;
(b) obtaining mRNA from a cell;
(c) contacting the mRNA with the substrate bound unique molecular labeled capture oligonucleotide;
(d) reverse transcribing the mRNA;
(e) optionally amplifying the reverse transcribed mRNA;
(f) analyzing the sequence of the reverse transcribed mRNA; and
(g) identifying or cross-referencing the cell associated with the mRNA using the sequence and unique molecular label.

Clause 42. Use of the methods of clauses 1-33, the means or methods of clauses 39-40, or the compositions of clauses 34-38 for the capture and analysis of mRNA.

EXAMPLES

Synthesis of Unique Barcoded Sequences on Beads

The methods described herein to create barcoded sequences on substrates or beads involve synthesizing the sequence on the beads in a sequential fashion. Typical beads are 20 μm poly(styrene-divinylbenzene; PS-DVB) derivatized with hydroxyl, carboxyl, amine, aldehyde, or sulfate moieties for coupling with nucleic acids.

The beads used for these experiments were sourced from EPRUI Biotech Co. Ltd (Shanghai). They were 20 μm, 1000 Å pore size, hydroxy functionalized PS-DVB beads (1-005-20-1000). The template oligonucleotide sequence was:

(SEQ ID NO: 32)
5'-Am-mSp18-TTTTTTTAAGCAGTGGTATCAACGCAGAGTAC-3', where "5'-Am" indicates a 5'-amino moiety and "mSp18" is a methylated hexaethylene glycol moiety (discussed below). Several other sequences were tested, including longer sequences as shown in Table 1.

TABLE 1

Exemplary Template Anchor DNA Sequences

| SEQ ID NO. | Name | Sequences (5'→3') |
|---|---|---|
| 32 | Template Anchor-1 | Am-mSp18-TTTTTTTAAGC AGTGGTATCAACGCAGAGTAC |
| 33 | Template Anchor-2 | TTTTTTTAAGCAGTGG TATCAACGCAG |
| 34 | Template Anchor-3 | TATTAATTAATATUAAGCAG TGGTATCAACGCAGAGTAC |

The sequence is DNA. An optional deoxyribouridine is shown as an underlined U.

The template oligonucleotide contains a 5'-amino modifier that was used to attach the oligo to the linker via standard N-hydroxysuccinimide (NHS)-ester chemistry. Phosphoramidite chemistry was used to construct the linker on the surface of the bead and to attach the NHS-ester containing molecule to the linker. The internal components of the linker include spacer 18 groups (Sp18, hexaethylene glycol) or optionally a 12-carbon chain is used for both the internal components of the linker as well as the NHS-ester amidite. Also, in place of the typical cyanoethyl protecting group, other protecting groups such as a methyl group may be used on the hexaethylene glycol amidites.

Commercially available beads of a similar size (~20 μm) can be used for these constructs. Beads from EPRUI Biosciences and Rapp Polymere (POLYSTYRENE M OH, Part number HM12000; TENTAGEL M OH, Part number M30200) can be used. Other substrates or beads including, gass, plastic, or hydrogels can also be used.

Figure 2A:
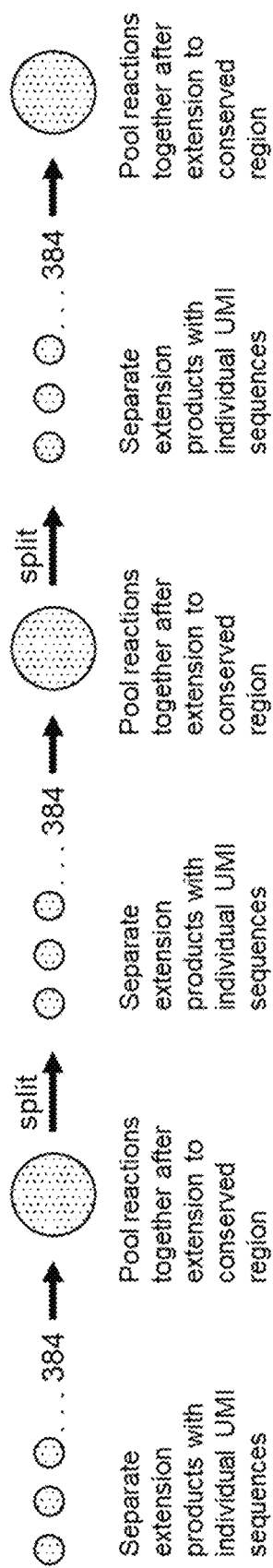
FIG. 2A shows diagram of the sequential addition of barcodes to beads. In this example, 384 different extension reactions are performed, followed by combination, separation, and repeat of the reaction until the desired result is achieved.
Figure 2B:
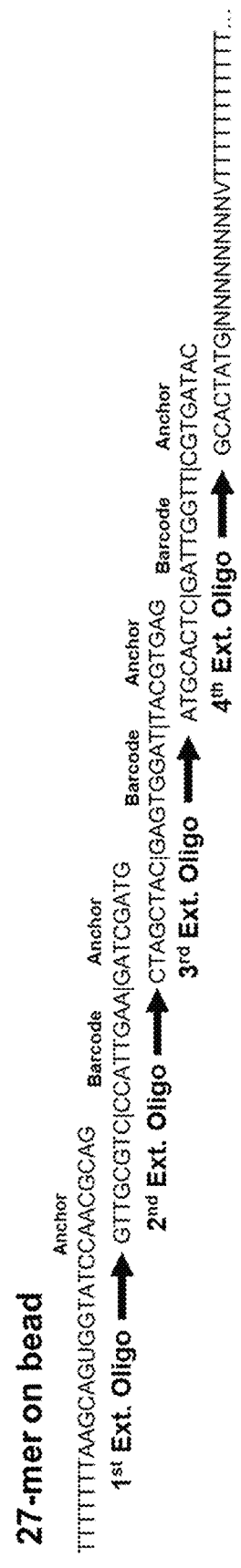
FIG. 2B shows example sequences and indicates how the barcodes are built up with repeated separate reactions, followed by mixing. The anchor oligonucleotide is attached to the bead, and the multiple first antisense extension oligonucleotides are annealed in separate reactions to the anchor. Extension across the antisense oligonucleotides generates the new conserved anchor point for the subsequent antisense extension oligonucleotide. After extension, combining of the different reactions, washing away of the antisense oligonucleotide liberates the newly synthesized anchor sequence for binding to the subsequent extension oligonucleotide in multiple separate extension reactions. After binding the next antisense extension oligonucleotide, the bead-attached sequence is extended again. The combining and washing steps were carried out in subsequent rounds, and a final separation and extension with the next antisense oligonucleotide was performed. Combining and washing of this step is followed by a single large reaction of all the beads and the final antisense extension oligonucleotide. This synthesis route intended to be exemplary and not restrict the number of rounds, the lengths of the primers or the sequences thereof.
Figure 2B:
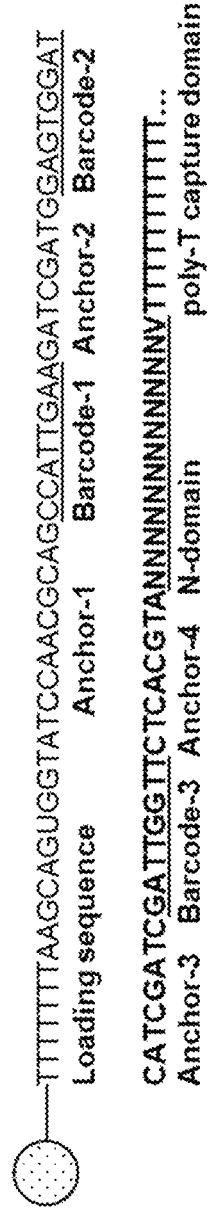

The first extension reaction was performed in multiple individual reactions in 1× reaction buffer (50 mM NaCl, 10 mM Tris·HCl, 10 mM MgCl$_2$, 1 mM DTT, pH 7.9, 25°) C., supplemented with 2 mM additional MgCl$_2$, 2.5 mM dNTP, an antisense oligonucleotide (e.g., as shown in Table 2, SEQ ID NO: 1-10) at a minimum of 3× the concentration of the extendable template on the beads, and the beads with the extendable template themselves. In this example, 10 separate antisense sequence were used for templates in the extension reactions. This is exemplary, and those with ordinary skill in the art will appreciate that a plurality of separate reactions can be used with alternative barcode or anchor sequences (FIG. 2A-C). In one embodiment, the number of reactions in each step is 384, for compatibility with high-throughput platforms.

Figure 3:
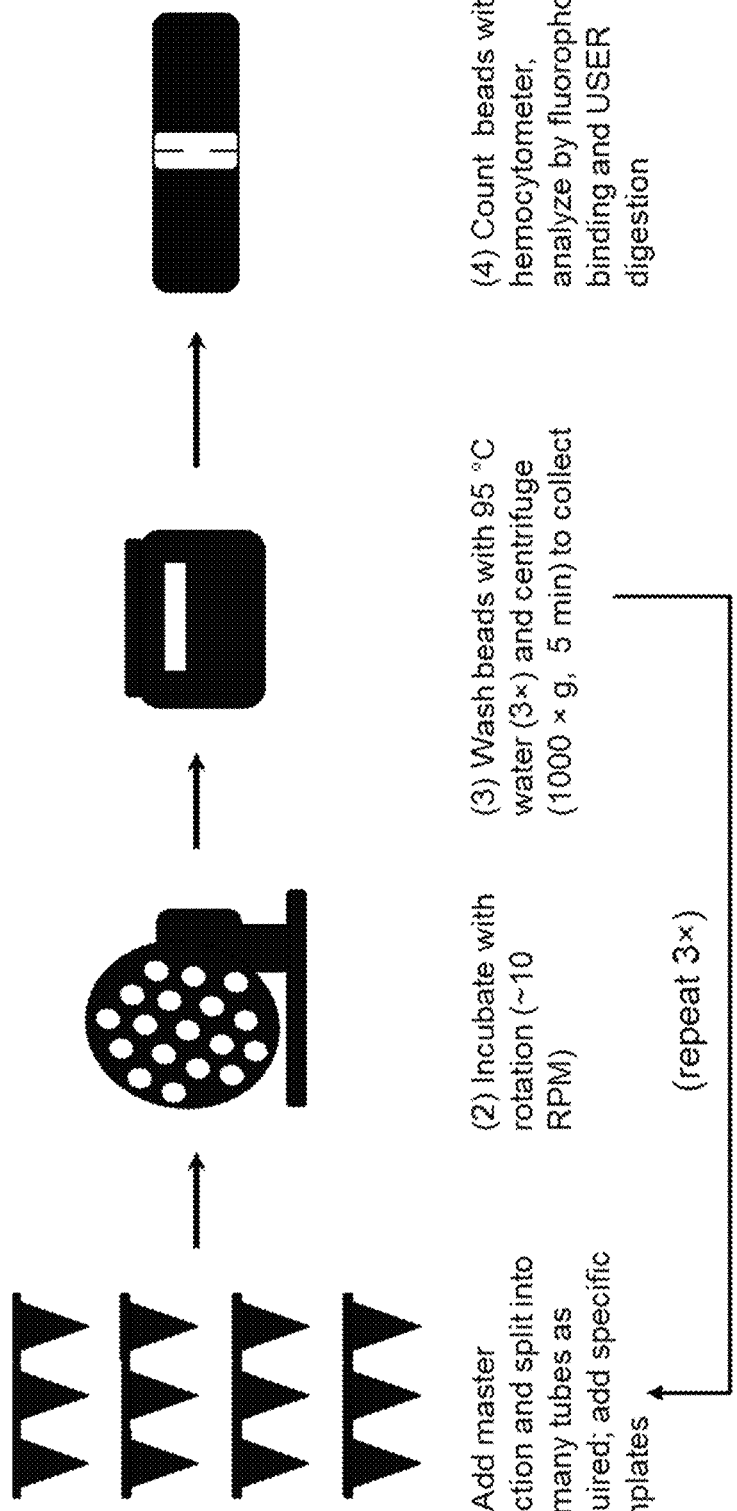
FIG. 3 shows the steps involved in barcoded bead synthesis. (1) The separate reactions were assembled (2) and incubated with rotation at room temperature to allow for extension across the antisense templates. (3) A washing step with 95° C. water and centrifugation were performed three times and permits successive extension steps to be conducted for a total of four rounds as shown in the examples. (4) The extended sequences attached to the beads were quantified by fluorophore binding and USER enzyme digestion.

To calculate the volume for these reactions, the concentration of the beads should not exceed 30 mg/mL of reaction mix. In one embodiment, this concentration does not exceed 20 mg/mL. The reaction was allowed to equilibrate at room temperature with mixing at ~10 RPM for at least 1 hour before the enzymatic components were added. After about 1 hr, E. coli DNA polymerase Klenow fragment (5'→3'/3'→5' Exo-) polymerase (New England Biolabs, Ipswich, MA; "NEB") was added to the reaction at a minimum concentration of 1 U/nmol of extendable template on the beads. In one embodiment, the concentration was 10 U of Klenow polymerase per nmol of template. E. coli inorganic pyrophosphatase (NEB) was also added to the reaction at a concentration of 1 unit per nmol of extendable template. The reaction was incubated with rotation at 10 to 20 RPM overnight to allow for the extension reaction to complete (FIG. 3, Steps 1-2).

TABLE 2

Exemplary Antisense Template Sequences for the First Extension

| SEQ ID NO. | Name | Sequences (5'→3') |
|---|---|---|
| 1 | AS 1.1 | CATCGATCTTCAATGGGTACTCTG-x |
| 2 | AS 1.2 | CATCGATCCGGAAATCGTACTCTG-x |
| 3 | AS 1.3 | CATCGATCGTGCGACTGTACTCTG-x |
| 4 | AS 1.4 | CATCGATCAGACTAGAGTACTCTG-x |
| 5 | AS 1.5 | CATCGATCGGTTAGGTGTACTCTG-x |
| 6 | AS 1.6 | CATCGATCAATGTTCCGTACTCTG-x |
| 7 | AS 1.7 | CATCGATCGGTTCCTCGTACTCTG-x |
| 8 | AS 1.8 | CATCGATCAGCAAGAAGTACTCTG-x |

TABLE 2-continued

Exemplary Antisense Template Sequences for the First Extension

| SEQ ID NO. | Name | Sequences (5'→3') |
|---|---|---|
| 9 | AS 1.9 | CATCGATCAGCACGTAGTACTCTG-x |
| 10 | AS 1.10 | CATCGATCGCGACTCTGTACTCTG-x |

Sequences shown in bold are complementary to the 3'-terminus of the anchor oligonucleotide, allowing for annealing and further extension across the antisense template. Sequences that are shown underlined are the antisense sequence of the second conserved "anchor" domain. The region between the bold and underlined sequences is the barcode region. It is shown here as 8 nucleotides but may be of any desired length. All sequences are DNA except for-x, which is a 3'-blocker to prevent efficient extension from the 3'-terminus of the antisense template. In one embodiment, this blocker is a C3 (1,3-propanediol) spacer.

Figure 4:
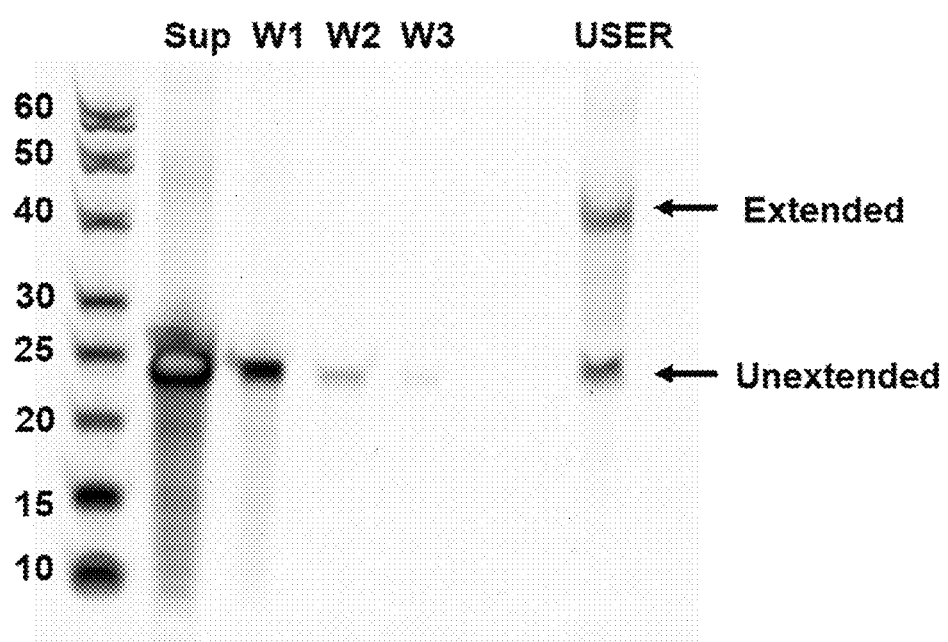
FIG. 4 shows an example of washing and analysis of extension by digestion with the USER enzyme (New England Biolabs, Ipswich, MA). The 5 μL of the supernatant and each of the three washes from the extension reactions (Sup, W1, W2, and W3) were loaded onto a denaturing 8 M urea 15% polyacrylamide gel for analysis. These were run at 300 volts for approximately 30-45 minutes and stained with a fluorescent DNA dye (GelRed). The band at 24 nucleotides was the combined antisense templates, and the decrease shows that they were washed away by the 95° C. wash steps. The USER lane represents 10 μL of the extended beads, digested with 10 Units of the USER enzyme overnight at room temperature. A 10 μL aliquot of this reaction was loaded onto the gel. The unextended template ran at 25 nucleotides and the extended template ran at 41 nucleotides.

After extension across the first antisense sequence oligonucleotides, the reactions were combined into a single tube or beaker and washed three times (3×) with at least 1× final combined volume 95° C. dH$_2$O (FIG. 3, Step 3). For each wash, the beads were sedimented in a centrifuge at a maximum of 1000× g for at least 1 minute, and the supernatant was removed and discarded. Fresh 95° C. dH$_2$O was added to the beads, and the process was repeated three times. This removed the majority (>99%) of the antisense oligonucleotides from the beads and permitted quantitation of the extension product and the second extension reaction (FIG. 4 and Example 2).

After washing, the total volume of suspended beads and the solution was determined. This volume was divided by the total number of reactions and a volume was calculated. Aliquots of the calculated volume were dispensed into individual cells of plates for the next extension reactions.

The second extension reaction was performed in multiple individual reactions in 1× reaction buffer (50 mM NaCl, 10 mM Tris. HCl, 10 mM MgCl$_2$, 1 mM DTT, PH 7.9, 25°) C., supplemented with 2 mM additional MgCl$_2$, 2.5 mM dNTP, an antisense oligonucleotide (e.g., as shown in Table 3, SEQ ID NO: 11-20) at a minimum concentration of 3× the concentration of the extendable template on the beads, and the beads with the extendable template themselves. To calculate the volume in which to perform these reactions, the concentration of the beads should not exceed 30 mg/ml of reaction mix. In one embodiment, the concentration does not exceed 20 mg/mL. The reaction was allowed to equilibrate at room temperature with mixing of about ~10 RPM for at least 1 hr before the enzymatic components were added. After an hour, *E. coli* DNA polymerase Klenow fragment (Exo$^-$) was added at minimum concentration of 1 U per nmol of extendable template on the beads. In one embodiment, the concentration of Klenow polymerase is 10 U per nmol of template. *E. coli* inorganic pyrophosphatase (NEB) was also added at a concentration of 1 unit per nmol of extendable template. The reaction was incubated with rotation at ~10-20 RPM overnight to allow the extension reaction to run to completion (see FIG. 3, Steps 1-2).

TABLE 3

Exemplary Antisense Template Sequences for the Second Extension

| SEQ ID NO. | Name | Sequences (5'→3') |
|---|---|---|
| 11 | AS 2.1 | CTCACGTAATCCACTCCATCGATC-x |
| 12 | AS 2.2 | CTCACGTACGATCTTACATCGATC-x |
| 13 | AS 2.3 | CTCACGTACTCGTGAACATCGATC-x |
| 14 | AS 2.4 | CTCACGTATGAATGCGCATCGATC-x |
| 15 | AS 2.5 | CTCACGTAGTTAGATCCATCGATC-x |
| 16 | AS 2.6 | CTCACGTATAAGTCCACATCGATC-x |
| 17 | AS 2.7 | CTCACGTACTAGCGAACATCGATC-x |
| 18 | AS 2.8 | CTCACGTACGCATTTCCATCGATC-x |
| 19 | AS 2.9 | CTCACGTACAGGTGTACATCGATC-x |
| 20 | AS 2.10 | CTCACGTAGGTCAACGCATCGATC-x |

Sequences shown in bold are complementary to the 3'-terminus of the extending oligonucleotide, allowing for annealing and further extension across the antisense template. Sequences that are shown underlined are the antisense sequence of the third conserved "anchor" domain. The region between the bold and underlined sequences is the barcode region. It is shown here as 8 nucleotides but may be of any desired length. All sequences are DNA except for-x, which is a 3'-blocker to prevent efficient extension from the 3'-terminus of the antisense template. In one embodiment, this blocker is a C3 (1,3-propanediol) spacer.

After extension across the second antisense sequence oligonucleotides, the reactions were combined again, and washed three times (3×) with at least 1× final combined volume 95° C. dH$_2$O. For each wash, the beads were sedimented in a centrifuge at a maximum of 1000× g for at least 1 minute, and the supernatant was removed and discarded. Fresh 95° C. dH$_2$O is added to the beads, and the process was repeated three times. This removed the majority (>99%) of the antisense oligonucleotides from the beads and permitted quantitation of the extension product (see FIG. 4 and Example 2), and the third extension reaction (FIG. 3, Step 3).

As before, the total volume of beads and the suspension solution was determined after washing. This volume was divided by the total number of reactions and a volume was calculated. Aliquots of the calculated volume were dispensed into individual cells of plates for the next extension reactions.

The third extension reaction was performed in multiple individual reactions in 1× reaction buffer (50 mM NaCl, 10 mM Tris. HCl, 10 mM MgCl$_2$, 1 mM DTT, PH 7.9, 25°) C., supplemented with 2 mM additional MgCl$_2$, 2.5 mM dNTP, an antisense oligonucleotide (as shown in Table 4, SEQ ID NO: 21-30) at a minimum of 3×the concentration of the extendable template on the beads, and the beads with the extendable template themselves. To calculate the volume in which to perform these reactions, the concentration of the beads should not exceed 30 mg/ml of reaction mix. In one embodiment this concentration did not exceed 20 mg/mL. The reaction was allowed to equilibrate at room temperature with mixing of ~10 RPM for at least 1 hour before enzymatic components were added. After about 1 hour, *E. coli* DNA polymerase Klenow fragment (Exo$^-$) (NEB) was added at minimum concentration of 1 U per nmol of extendable template on the beads. In one embodiment, the concentration of Klenow polymerase is 10 U per nmol of template. *E. coli* inorganic pyrophosphatase (NEB) was also added at a concentration of 1 unit per nmol of extendable template. The reaction is then incubated with rotation at 10 to 20 RPM overnight to allow for the extension reaction to complete (FIG. 3, Steps 1-2).

TABLE 4

Exemplary Antisense Template Sequences for the Third Extension

| SEQ ID NO. | Name | Sequences (5'→3') |
|---|---|---|
| 21 | AS 3.1 | GTATCACGAACCAATCCTCACGTA-x |
| 22 | AS 3.2 | GTATCACGCACCAAGGCTCACGTA-x |
| 23 | AS 3.3 | GTATCACGTTTCCAACCTCACGTA-x |
| 24 | AS 3.4 | GTATCACGTCCGAATGCTCACGTA-x |
| 25 | AS 3.5 | GTATCACGGCAATTGACTCACGTA-x |
| 26 | AS 3.6 | GTATCACGAACCTAGACTCACGTA-x |
| 27 | AS 3.7 | GTATCACGCATTCAGTCTCACGTA-x |
| 28 | AS 3.8 | GTATCACGGCGCATTTCTCACGTA-x |
| 29 | AS 3.9 | GTATCACGCACTTACGCTCACGTA-x |
| 30 | AS 3.10 | GTATCACGCATGTTCGCTCACGTA-x |

Sequences shown in bold are complementary to the 3'-terminus of the extending oligonucleotide, allowing for annealing and further extension across the antisense template. Sequences that are shown underlined are the antisense sequence of the fourth conserved "anchor" domain. The region between the bold and underlined sequences is the barcode region. It is 8 nucleotides in the primers above but may be of any desired length. All sequences are DNA except for-x, which is a 3'-blocker to prevent efficient extension from the 3'-terminus of the antisense template. In one embodiment, this blocker is a C3 (1,3-propanediol) spacer.

After extension across the third antisense sequence oligonucleotides, the reactions are combined again, and washed three times (3×) with at least 1× final combined volume 95° C. dH₂O. For each wash, the beads are sedimented in a centrifuge at a maximum of 1000× g for at least 1 minute, and the supernatant is drawn off from the beads. Fresh 95° C. dH₂O is added to the beads, and the process is repeated three times. This will remove the vast majority (>99%) of the antisense oligonucleotides from the beads and allow for quantification of extension (see FIG. 4 and Example 2), as well as the fourth and final extension reaction (FIG. 3, Step 3).

After washing, the total volume of beads suspended in solution was determined. This volume was divided by the total number of reactions and a volume was calculated. Aliquots of the calculated volume were dispensed into individual cells of plates for the next extension reactions.

The fourth and final extension reaction is performed as a single reaction in 1×reaction buffer (50 mM NaCl, 10 mM Tris. HCl, 10 mM MgCl₂, 1 mM DTT, PH 7.9, 25°) C., supplemented with 2 mM additional MgCl₂, 5 mM dNTP, an antisense oligonucleotide (such as what is shown in Table 5, SEQ ID NO: 31) at a minimum of 3× the concentration of the extendable template on the beads, and the beads with the extendable template themselves. To calculate the volume in which to perform these reactions, the concentration of the beads should not exceed 30 mg/ml of reaction mix (in one embodiment this concentration does not exceed 20 mg/mL). The reaction is allowed to equilibrate at room temperature with mixing of at least 10 RPM for at least 1 hour before enzymatic components are added. After about 1 hour, *E. coli* DNA polymerase Klenow fragment (Exo-) (NEB) was added at minimum concentration of 1 U per nmol of extendable template on the beads. In one embodiment, the concentration of Klenow polymerase is 10 U per nmol of template. *E. coli* inorganic pyrophosphatase (NEB) was also added at a concentration of 1 unit per nmol of extendable template. The reaction is then incubated with rotation at 10 to 20 RPM overnight to allow for the extension reaction to finish (FIG. 3, Steps 1-2).

Following the final extension, the antisense oligonucleotide was removed using 95° C. dH₂O as described in the previous steps (FIG. 3, Step 3). The final extended barcoded beads can be quantified using techniques described in FIG. 3, Step 4, and Example 2.

TABLE 5

Exemplary Antisense Template Sequences for the Fourth Extension

| SEQ ID NO. | Name | Sequence (5'→3') |
|---|---|---|
| 31 | AS 4.1 | AAAAAAAAAAAAAAAAAAAAAAAAA AAAABNNNNNNNNNNNNNGTATCACG-x |

Sequences shown in bold are complementary to the 3'-terminal anchor domain of the extending oligonucleotide, allowing for annealing and further extension across the antisense template. N is any nucleotide, and B is any nucleotide except A. The region of the N-nucleotides is a unique molecular index for individual mRNA capture events. It is shown here as 12 nucleotides but may be of any desired length. All sequences are DNA except for-x, which is a 3'-blocker to prevent efficient extension from the 3'-terminus of the antisense template. In one embodiment, the blocker on the 3'-terminus is a C3 (1,3-propanediol) spacer.

An exemplary sequence produced by the process described herein is shown (SEQ ID NO: 38):

```
5'-TATTAATTAATATUAAGCAGTGGTATCAACGCAGAGTACXXXXXXXXGATCGATGXXXXXXXX
Loading sequence            Anchor-1     Barcode-1 Anchor-2 Barcode-2

CATCGATCXXXXXXXXCTCACGTANNNNNNNNNNNNNVTTTTTTTTTTTTTTTTTTTTTT...-3'
Anchor-3 Barcode-3  Anchor-4 N-domain  poly-T capture domain
```

A specific example sequence produced by the process described herein and shown in FIG. 2C is shown (SEQ ID NO: 39):

```
5'-TATTAATTAATATUAAGCAGTGGTATCAACGCAGAGTACCCATTGAAGATCGATGGAGTGGAT
Loading sequence            Anchor-1 Barcode-1 Anchor-2 Barcode-2

TACGTGAGGATTGGTTCGTGATACNNNNNNNNNNNNNVTTTTTTTTTTTTTTTTTTTTT...-3'
Anchor-3 Barcode-3  Anchor-4 N-domain  poly-T capture domain
```

Another specific example sequence produced by the process described herein is shown (SEQ ID NO: 40):

```
5'-TATTAATTAATATUAAGCAGTGGTATCAACGCAGAGTACCCATTGAAGATCGATGGAGTGGAT
   Loading sequence  Anchor-1 Barcode-1 Anchor-2 Barcode-2

CATCGATCGATTGGTTCTCACGTANNNNNNNNNNNNNVTTTTTTTTTTTTTTTTTTTTTTTT...-3'
Anchor-3 Barcode-3 Anchor-4 N-domain poly-T capture domain
```

Another example sequence produced by the process described herein is shown (SEQ ID NO: 41):

```
5'-TTTTTTTAAGCAGUGGTATCCAACGCAGCCATTGAAGATCGATGGAGTGGAT
   Loading Nucleotide Anchor-1   Barcode-1 Anchor-2 Barcode-2

CATCGATCGATTGGTTCTCACGTANNNNNNNNNNNNNVTTTTTTTTTTTTTTTTTTTTTTTT...-3'
Anchor-3 Barcode-3 Anchor-4 N-domain poly-T capture domain
```

Example 2

Quantitation of the Template Oligonucleotide Loading on the Beads

Also described herein are methods for orthogonally quantifying both the initial attachment of the anchor oligonucleotide to the beads, and the efficiency of each extension reaction. This was accomplished using multiple techniques.

The quantification of the number of beads/µL in solution is done using a mammalian cell-counting hemocytometer, using techniques that are known to those with skill in the art (FIG. 3, Step 4). Briefly, 10 µL of diluted beads are placed onto the hemocytometer, and the number of beads visible in four different defined sectors were counted, and averaged. This number was multiplied by 10× (to obtain the number of beads/µL), and then by the dilution factor to obtain the original bead concentration in beads/µL. This is multiplied by 1000 and is divided by 300,000 (the number of beads in one mg) to obtain the mg/mL bead concentration.

Example 3

Quantitation of the Extension on the Beads

A method for quantifying the extension on beads is by digesting the extended and unextended sequences using the USER enzyme (NEB). This enzyme digests both single stranded and double stranded DNA that contains a deoxyuracil. A template anchor sequence that contains a deoxyuracil (see Table 6, SEQ ID NO: 33-34) can be cleaved by this enzyme, separating it from the bead.

TABLE 6

Exemplary Template Anchor DNA Sequences

| SEQ ID NO. | Name | Sequences (5'→3') |
|---|---|---|
| 32 | Template Anchor-1 | Am-mSp18-TTTTTTTAAGC AGTGGTATCAACGCAGAGTAC |
| 33 | Template Anchor-2 | TTTTTTTAAGCAGUGGTATC AACGCAG |
| 34 | Template Anchor-3 | TATTAATTAATATUAAGCAG TGGTATCAACGCAGAGTAC |

The sequence is DNA. An optional deoxyribouridine is shown as an underlined U.

To quantify the percentage of extension after the reactions performed in each step described in Example 1, 10 µL of washed beads are added to a solution containing 25 µL dH$_2$O, 5 µL of 10× Cutsmart™ buffer (NEB), and 10 units (10 µL) of USER™ enzyme (50 µL total). The reaction was incubated with rotation at >10 RPM overnight at either room temperature or 37° C. The resulting solution was centrifuged at 1000×g for ~1 minute, and the supernatant was removed. 10 µL of the resulting product was run on a denaturing 8 M urea, 15% polyacrylamide gel at 300 volts for approximately 30 to 45 minutes (FIG. 4). After staining with GelRed™ or an equivalent fluorescent DNA dye, quantification of the extended and unextended products was performed using standard techniques.

Example 4

Fluorescence Quantification of Loading and Extension Products

Quantification of the template anchor sequence synthesized on the beads or the amount extended at each step can be performed by fluorescence analysis of the beads. Fluorescent analysis was performed by annealing a fluorescently quenched probe to the sequence of interest, resulting in a separation of the fluorophore and quencher, and generating a fluorescent signal. This signal was compared against a standard curve of off-bead oligonucleotide identical to the sequence of interest. From this, the total amount of DNA on the beads was quantified.

To perform fluorescent quantification of the DNA on the beads, dilutions between 400 and 2,000 beads/µL were conducted using TE (10 mM Tris·HCl, 1 mM EDTA, pH 8) or dH$_2$O. Fluorescently quenched oligonucleotide probes are shown in Table 6, SEQ ID NO: 33 and 35. These probes typically have a random coil design (SEQ ID NO: 33), or a hairpin (SEQ ID NO: 35). The sequences are not intended to be the only potential designs but are exemplary. Control sequences for the standard curve were also designed (e.g., SEQ ID NO: 34 or 32).

TABLE 7

Exemplary Fluorescent Quantification Probes and Standard Curve Reagents

| SEQ ID NO. | Name | Sequence |
|---|---|---|
| 35 | Load quant | F-CTGCGTTGATACCACTG-Q |
| 36 | Full Ext curve | TTTTTTTTTTTTTTTTTTTT |
| 37 | Poly A HP quant | F-CTAGTAAAAAAAAAAAAAA AACTAG-Q |

All sequences are DNA. F is 5'-fluorescein or an equivalent fluorophore, and Q is Iowa Black™ Fluorescent Quencher or an equivalent quencher.

To make the standard curve, dilutions of 16 µmol/µL (16 µM), 8 µmol/µL (8 µM), 4 µmol/µL (4 µM), and 2 µmol/L (2

µM) were prepared using the control template(s) (Tables 4 and 5, SEQ ID NO: 32 or 34). A 5 µL aliquot of each of these dilutions (e.g., 80 µmol; 40 µmol; 20 µmol; 10 µmol, or 0 µmol) are added to reactions containing 0.5×Cutsmart™ buffer (NEB), and 100 µmol of the fluorescent probe (SEQ ID NO: 33 or 35) in a total reaction volume of 100 µL. All reactions were performed in triplicate to ensure accuracy. These reactions were placed into Corning Costar 96-well black, clear flat-bottom plates (Corning, Kennebunk, ME).

A 5 µL aliquot of the bead dilutions (approximately 2,000 to 10,000 beads over the dilution range) were added to individual reactions containing 0.5× Cutsmart™ buffer (NEB), and 100 µmol of the fluorescent probe (SEQ ID NO: 34 or 36) in a total reaction volume of 100 µL. These reactions were placed into the same Corning Costar® 96-well black, clear flat-bottom plates (Corning, Kennebunk, ME) (in different wells) that contained the standard curve.

The beads and fluorophore were incubated covered in the dark for a minimum of 2 hours at room temperature to allow annealing of the fluorophore to the beads. The fluorescence was measured on a TECAN® Spark 10M (or equivalent instrument). Measurement parameters include excitation at 485 nm, and emission at 535 nm. About 30 flashes were taken, and the gain was calculated from one of the wells with the 80 µmols of standard curve template DNA. The Z-position was fixed at 17,500 µm, and reads were observed from the top.

Once the fluorescence data were obtained, a standard curve is plotted, and the linear regression line formula was obtained. This formula was used to calculate the number of µmol of DNA in the bead reactions. By dividing the µmol of DNA by the number of beads and multiplying by 1000, the amount of fmol of DNA per bead was calculated.

Given that ~300,000 beads are in 1 mg of beads, 3.25 fmol of DNA/bead is equivalent to 1 nmol/mg. The number of fmol DNA/bead obtained can be divided by 3.25 to obtain the number of nmol/mg. The formula is shown in Formula 1:

$$\frac{DNA\ f\text{mol}}{\text{bead}} = \left(\frac{n\text{mol}\ DNA}{\text{mg bead}}\right) = \frac{\left(\frac{p\text{mol}\ DNA}{\text{no. beads}} \times 1000\right)}{3.25\ f\text{mol}\ DNA/\text{bead}}$$

From these orthogonal techniques, quantitation of both the bead anchor loading and extension products were determined and confirmed.

What is claimed:

1. A method for preparing a unique molecular labeled substrate, the method comprising:
   (a) providing a substrate comprising one or more oligonucleotide templates attached to the substrate, wherein the substrate is a bead, derivatized bead, derivatized glass slide, or derivatized polymer;
   (b) adding a primer template partially complementary to the one or more oligonucleotide templates; wherein:
      the primer template comprises a single stranded oligonucleotide having a structure comprising:

5'-Antisense-$N_{8-20}$-Barcode-$N_{8-20}$-Anchor-$N_{4-20}$-x-3', where:
      Antisense-$N_{8-20}$ is an antisense sequence of 8 to 20 nucleotides complementary to an anchor sequence of the oligonucleotide template or the extended product;
      Barcode-$N_{8-20}$ is a barcode region of 8 to 20 nucleotides;
      Anchor-$N_{4-20}$ is an anchor sequence of 4 to 20 nucleotides; and
      -x is a 3'-blocking moiety to prevent extension from the 3'-terminus of the primer template;
   (c) adding reagents sufficient to perform an extension reaction;
   (d) incubating the extension reaction for a period of time sufficient to produce an extension product;
   (e) purifying the substrate comprising the extension product;
   (f) repeating steps (b) to (e) at least two additional times using additional primer templates partially complementary to the extended product from each subsequent round;
   (g) purifying the substrate comprising the final extension product using the same process as in step (e); and
   (h) optionally, quantitating the amount of the oligonucleotide templates attached to the substrate, the amount of extension product attached to the substrate at each round, or the amount of the final extension product attached to the substrate.

2. The method of claim 1, wherein a plurality of reactions is performed simultaneously using different primer templates partially complementary to the one or more oligonucleotide templates in step (b) and the additional primer templates partially complementary to the extended product from each subsequent round in step (f).

3. The method of claim 2, wherein at least 2, 8, 12, 16, 24, 48, 96, 192, 384, 768, 1536, or more reactions are performed simultaneously.

4. The method of claim 1, wherein the one or more oligonucleotide templates in step (a) comprises a conserved anchor sequence.

5. The method of claim 1, wherein the one or more oligonucleotide templates in step (a) comprises at least one deoxyuridine nucleotide.

6. The method of claim 1, wherein the one or more oligonucleotide templates in step (a) comprise a single stranded oligonucleotide have a structure comprising:

Substrate-Template-$N_{20-50}$-Anchor-$N_{4-20}$, wherein:
   Substrate is an inert substrate;
   Template-$N_{20-50}$ is a template sequence of 20 to 50 nucleotides optionally comprising at least one deoxyuridine nucleotide; and
   Anchor-$N_{4-20}$ is an anchor sequence of 4 to 20 nucleotides.

7. The method of claim 1, wherein the one or more oligonucleotide templates in step (a) comprise a single stranded oligonucleotide have a structure comprising:

Substrate-Template-$N_{20-50}$-Anchor-$N_{8-20}$, wherein:
   Substrate is an inert substrate;
   Template-$N_{20-50}$ is a template sequence of 20 to 50 nucleotides optionally comprising at least one deoxyuridine nucleotide; and
   Anchor-$N_{8-20}$ is an anchor sequence of 8 to 20 nucleotides.

8. The method of claim 1, wherein the primer template partially complementary to the one or more oligonucleotide templates in step (b) and the additional primer templates partially complementary to the extended product from each subsequent round in step (f) each comprise one or more unique barcodes and one or more conserved anchor sequences.

9. The method of claim 1, wherein the additional primer templates partially complementary to the extended product from each subsequent round in step (f) comprise a single stranded oligonucleotide having a structure comprising:

5'-Antisense-$N_{8-20}$-Barcode-$N_{8-20}$-Anchor-$N_{4-20}$-X-3', wherein:
   Antisense-$N_{8-20}$ is an antisense sequence of 8 to 20 nucleotides complementary to an anchor sequence of the oligonucleotide template or the extended product;
   Barcode-$N_{8-20}$ is a barcode region of 8 to 20 nucleotides;
   Anchor-$N_{4-20}$ is an anchor sequence of 4 to 20 nucleotides; and
   -x is a 3'-blocking moiety to prevent extension from the 3'-terminus of the primer template.

10. The method of claim 1, wherein the primer template partially complementary to the one or more oligonucleotide templates in step (b) and the additional primer templates partially complementary to the extended product from each subsequent round in step (f) comprise a single stranded oligonucleotide having a structure comprising:

5'-Antisense-$N_{8-20}$-Barcode-$N_{8-20}$-Anchor-$N_{8-20}$-x-3', wherein:
Antisense-$N_{8-20}$ is an antisense sequence of 8 to 20 nucleotides complementary to an anchor sequence of the oligonucleotide template or the extended product;
Barcode-$N_{8-20}$ is a barcode region of 8 to 20 nucleotides;
Anchor-$N_{8-20}$ is an anchor sequence of 8 to 20 nucleotides; and
-x is a 3'-blocking moiety to prevent extension from the 3'-terminus of the primer template.

11. The method of claim 9, wherein the 3'-blocking moiety comprises 3'-TEG (triethylene glycol), 3'-SpC3 (1,3-propanediol), 3'-Sp18 (hexaethylene glycol), 3'-amino, 3'-phosphate, 3'-biotin, 3'-1',2'-dideoxyribose, 3'-dideoxycytidine, or 3'-inverted deoxythymidine.

12. The method of claim 1, wherein the primer template for the final primer extension reaction in step (f) comprises a poly $A_{10-30}$ tail.

13. The method of claim 1, wherein the primer template for the final primer extension reaction in step (f) comprises a poly $N_{8-20}$ region.

14. The method of claim 1, wherein the primer template for the final primer extension reaction in step (f) comprising a single stranded oligonucleotide having a structure comprising:

5'-$A_{10-30}$-B-$N_{8-20}$-Anchor $N_{4-20}$-X-3', wherein:
$A_{10-30}$ is a sequence of 10 to 30 deoxyadenosine residues;
B is a single deoxyguanosine, deoxycytidine, or deoxythymidine nucleotide;
$N_{8-20}$ is a sequence of any 8 to 20 nucleotides;
Anchor $N_{4-20}$ is an anchor sequence of 4 to 20 nucleotides; and
-x is a 3'-blocking moiety to prevent extension from the 3'-terminus of the primer template.

15. The method of claim 1, wherein the primer template for the final primer extension reaction in step (f) comprising a single stranded oligonucleotide having a structure comprising:

5'-$A_{10-30}$-B-$N_{8-20}$-Anchor $N_{8-20}$-X-3', wherein:
$A_{10-30}$ is a sequence of 10 to 30 deoxyadenosine residues;
B is a single deoxyguanosine, deoxycytidine, or deoxythymidine nucleotide;
$N_{8-20}$ is a sequence of any 8 to 20 nucleotides;
Anchor $N_{8-20}$ is an anchor sequence of 8 to 20 nucleotides; and
-x is a 3'-blocking moiety to prevent extension from the 3'-terminus of the primer template.

16. The method of claim 1, wherein the derivatization comprises hydroxyl, carboxyl, amine, aldehyde, or sulfate moieties for coupling with nucleic acids or modified nucleic acids.

17. The method of claim 16, wherein the modified nucleic acid comprises an amino-terminated oligonucleotide.

18. The method of claim 1, wherein the derivatized bead comprises natural or synthetic polymers or hydrogels, organic or inorganic particles, glass, ceramic, metal, paramagnetic particles, or combinations thereof.

19. The method of claim 1, wherein the derivatized bead comprises poly(styrene-divinylbenzene) derivatized with hydroxyl moieties.

20. The method of claim 1, wherein the substrate comprising one or more oligonucleotide templates has a concentration in the reaction of 10-40 mg/mL.

21. The method of claim 1, wherein the reagents sufficient to perform an extension reaction comprise: a buffered solution, deoxyribonucleotide triphosphates (dNTPs), a DNA polymerase, and optionally, a pyrophosphatase.

22. The method of claim 21, wherein the DNA polymerase is *E. coli* DNA polymerase Klenow fragment (Exo$^-$).

23. The method of claim 21, wherein the DNA polymerase is provided at a ratio of 1-10 U per nmol of oligonucleotide template.

24. The method of claim 21, wherein the optional pyrophosphatase is provided at a ratio of 1 U pyrophosphatase per nmol of oligonucleotide template.

25. The method of claim 1, wherein the period of time in step (d) comprises about 30 min to about 20 hours at a temperature of about 25° C. to about 37° C. with rotation of the extension reaction at 10-20 rpm.

26. The method of claim 1, wherein the purification in step (e) comprises combining the substrates comprising the extension products together, washing the combination with hot water or buffer, and collecting the substrate comprising the primer extension product by centrifugation.

27. The method of claim 26, wherein the purification step is performed at least 3 times.

28. The method of claim 1, wherein following the purification in step (e), the substrates comprising the extension products are diluted and redistributed into individual reactions.

29. The method of claim 1, wherein step (f) repeats steps (b) to (e) at least 3 to 100 times; each time using additional primer templates partially complementary to the extended product from each subsequent round.

30. The method of claim 1, wherein step (f) repeats steps (b) to (e) at least 3 times, 4 times, 5, times, 6 times, 7 times, 8 times, 9 times, 10 times, 20 times, 50 times, 100 times, or even more each time using additional primer templates partially complementary to the extended product from each subsequent round.

31. The method of claim 1, wherein the quantitating the amount of the oligonucleotide templates attached to the substrate, the amount of extension product attached to the substrate at each round, or the amount of the final extension product attached to the substrate comprises one or more of:

(a) calculating the concentration of the substrate comprising an oligonucleotide template, extension product, or final extension product in solution by diluting a solution of the substrate;
counting the number of substrates;
applying a dilution factor; and
obtaining a concentration of the substrate in solution;
or
(b) cleaving the oligonucleotide templates attached to the substrate, the amount of extension product attached to the substrate at each round, or the amount of the final extension product attached to the substrate with one or more enzymes that specifically cleave the phosphodiester linkage at deoxyuridine nucleotides; and
quantifying the amount of oligonucleotide templates attached to the substrate, the amount of extension product attached to the substrate at each round, or the amount of the final extension product attached to the substrate;
or
(e) diluting the substrate comprising the oligonucleotide template, the extension products after a round, or the final extension product;
preparing a serial dilution using control templates;

adding and annealing a fluorescently quenched probe oligonucleotide to the oligonucleotide template, the extension product, the final extension product, or the serially diluted control templates to obtain fluorescently labeled double stranded sequences;

measuring the fluorescence signal of the fluorescently labeled double stranded sequences;

preparing a standard curve of the fluorescence signal of the control templates; and using the standard curve and the fluorescence signal of the of the oligonucleotide template, the extension product, or the final extension product to quantitate the amount (mass or moles) of the oligonucleotide template, the extension product, or the final extension product; or a combination thereof.

32. The method of claim 31, wherein the one or more enzymes in step (b) comprises a mixture of uracil DNA glycosylase and DNA glycosylase-lyase Endonuclease VIII.

* * * * *